(12) United States Patent
Ingram et al.

(10) Patent No.: US 10,307,335 B2
(45) Date of Patent: Jun. 4, 2019

(54) FEMALE ENTERAL COUPLING

(71) Applicant: NEOMED, INC., Woodstock, GA (US)

(72) Inventors: Aaron N. Ingram, Canton, GA (US); Benjamin Martin Davis, Woodstock, GA (US); Anthony C. Lair, Alpharetta, GA (US); Mark Martin Costello, County Mayo (IE); Tony Doherty, County Mayo (IE)

(73) Assignee: NeoMed, Inc., Woodstock, GA (US)

( * ) Notice: Subject to any disclaimer, the term of this patent is extended or adjusted under 35 U.S.C. 154(b) by 788 days.

(21) Appl. No.: 14/613,136

(22) Filed: Feb. 3, 2015

(65) Prior Publication Data
US 2015/0164744 A1 Jun. 18, 2015

Related U.S. Application Data

(63) Continuation of application No. 13/600,595, filed on Aug. 31, 2012, which is a continuation-in-part of (Continued)

(51) Int. Cl.
*A61J 1/14* (2006.01)
*A61M 39/10* (2006.01)
(Continued)

(52) U.S. Cl.
CPC .............. *A61J 1/1475* (2013.01); *A61J 9/00* (2013.01); *A61J 15/0011* (2013.01); (Continued)

(58) Field of Classification Search
CPC .... A61J 1/1475; A61J 15/0011; A61J 1/1481; A61J 9/00; A61J 9/085; A61J 15/0076;
(Continued)

(56) References Cited

U.S. PATENT DOCUMENTS 2,303,997 A 12/1942 Hogg
2,972,991 A 2/1961 Burke
(Continued)

FOREIGN PATENT DOCUMENTS

EP 0278015 A1 8/1988
WO 2006105601 A1 10/2006

OTHER PUBLICATIONS

International Search Report and Written Opinion for PCT/US2012/053312; dated Jun. 13, 2013; 14 pgs.

*Primary Examiner* — Theodore J Stigell
(74) *Attorney, Agent, or Firm* — Gardner Groff Greenwald & Villaneuva P.C.

(57) ABSTRACT

A container for collecting, transporting, storing, delivering and dispensing fluid. The container has a hollow tube with an outer circumference diameter and is configured to receive a plunger. A collection adaptor and a dispensing adaptor provide interchangeable coupling of a variable volume container such as a syringe with a collection device such as a breast pump and a dispensing device such as a nipple. The container also has a circumferential seal assembly secured at one end of the hollow tube. The seal assembly outer diameter is substantially similar to the hollow tube outer diameter.

18 Claims, 18 Drawing Sheets

Related U.S. Application Data application No. 13/191,721, filed on Jul. 27, 2011, now Pat. No. 9,586,734.

(60) Provisional application No. 61/563,923, filed on Nov. 28, 2011.

(51) Int. Cl.
| | | |
|---|---|---|
| *A61J 15/00* | (2006.01) | |
| *A61M 5/162* | (2006.01) | |
| *A61M 5/178* | (2006.01) | |
| *A61J 9/00* | (2006.01) | |
| *B65D 83/00* | (2006.01) | |
| *B65D 47/08* | (2006.01) | |
| *B65D 47/20* | (2006.01) | |
| *A61M 5/31* | (2006.01) | |
| *A61J 9/08* | (2006.01) | |
| *A61J 11/00* | (2006.01) | |

(52) U.S. Cl.
CPC .......... *A61M 5/162* (2013.01); *A61M 5/1782* (2013.01); *A61M 39/10* (2013.01); *B65D 47/08* (2013.01); *B65D 47/2025* (2013.01); *B65D 47/2031* (2013.01); *B65D 83/0005* (2013.01); *A61J 9/085* (2013.01); *A61J 11/00* (2013.01); *A61J 15/0076* (2015.05); *A61M 2005/3123* (2013.01); *A61M 2039/1077* (2013.01)

(58) Field of Classification Search
CPC ............ A61J 11/00; A61M 2039/1077; A61M 39/10; A61M 5/162; A61M 5/1782; B65D 83/0005; B65D 47/08; B65D 47/2025; B65D 47/2031
See application file for complete search history.

(56) References Cited

U.S. PATENT DOCUMENTS

| | | | |
|---|---|---|---|
| 3,739,779 A * | 6/1973 | Pfleger | A61M 5/288 401/134 |
| 3,946,888 A | 3/1976 | Tonkin | |
| 4,010,861 A | 3/1977 | Welten | |
| 4,339,046 A | 7/1982 | Coen | |
| 4,493,348 A | 1/1985 | Lemmons | |
| 4,623,343 A | 11/1986 | Thompson | |
| 4,685,577 A | 8/1987 | Chen | |
| 4,898,291 A | 2/1990 | Sailors | |
| 5,035,340 A | 7/1991 | Timmons | |
| 5,125,415 A | 6/1992 | Bell | |
| 5,356,016 A | 10/1994 | Wiedemann | |
| 5,366,115 A | 11/1994 | Kersten et al. | |
| 5,423,791 A | 6/1995 | Bartlett | |
| 5,524,783 A | 6/1996 | Popoff | |
| 5,988,448 A | 11/1999 | Foth | |
| 6,050,432 A | 4/2000 | Koehnke | |
| 6,422,415 B1 | 7/2002 | Manganiello | |
| 6,465,024 B1 | 10/2002 | Di Scala et al. | |
| 6,511,457 B2 | 1/2003 | Thompson | |
| 6,666,852 B2 | 12/2003 | Niedospial, Jr. | |
| 6,732,872 B1 | 5/2004 | Gregro et al. | |
| 6,832,994 B2 | 12/2004 | Niedospial, Jr. et al. | |
| 7,032,764 B2 | 4/2006 | Viggiano | |
| 7,048,120 B2 * | 5/2006 | Pond | A61C 3/005 206/366 |
| 7,841,581 B2 | 11/2010 | Thorne, Jr. et al. | |
| 8,162,916 B2 | 4/2012 | Knight | |
| 8,231,597 B2 | 7/2012 | Knight | |
| 8,366,697 B2 | 2/2013 | Knight | |
| 8,979,819 B2 * | 3/2015 | Sherman | A61J 9/00 604/514 |
| 2002/0088827 A1 | 7/2002 | Colucci | |
| 2011/0054436 A1 | 3/2011 | Griffis, III et al. | |

\* cited by examiner

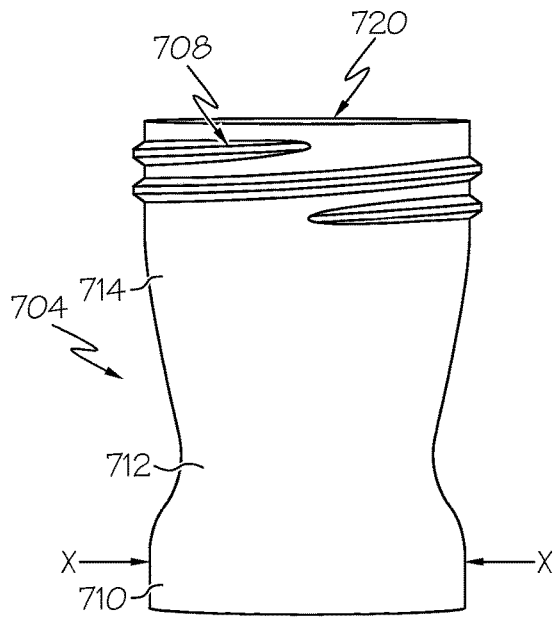
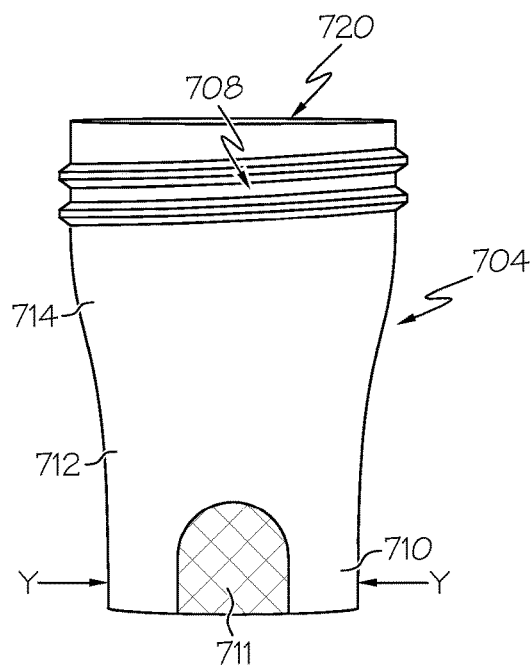
FIG. 24A  FIG. 24B
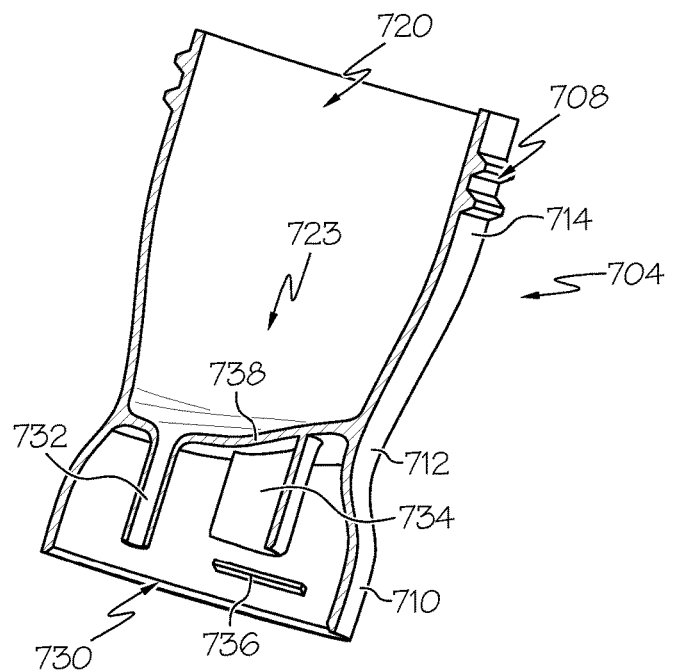
FIG. 25

FEMALE ENTERAL COUPLING

CROSS-REFERENCE TO RELATED APPLICATIONS

The present invention is a continuation of U.S. Non-Provisional patent application Ser. No. 13/600,595 filed Aug. 31, 2012, now abandoned, which claims priority to U.S. Provisional Patent Application Ser. No. 61/563,923 filed Nov. 28, 2011, and is a continuation-in-part of U.S. Non-Provisional patent application Ser. No. 13/191,721 filed Jul. 27, 2011, now U.S. Pat. No. 9,586,734 issued Mar. 7, 2017 which claims priority to U.S. Provisional Patent Application Ser. No. 61/368,023 filed Jul. 27, 2010, U.S. Provisional Patent Application Ser. No. 61/388,057 filed Sep. 30, 2010, and U.S. Provisional Patent Application Ser. No. 61/418,961 filed Dec. 2, 2010, the entireties of which are incorporated herein by reference.

TECHNICAL FIELD

The present invention relates generally to the field of collection and dispensing of fluids, and more particularly to a collection and dispensing system for biological fluids, such as breast milk and/or dietary or medicinal materials.

BACKGROUND

Maintaining aseptic integrity is of great importance in many fluid collection and dispensing applications. For example, in the delivery of breast milk or formula to premature infants who are unable to feed regularly, freshness and prevention of contamination are critical. The delivery of enteral fluids is often controlled by regulations and medical standards of practice.

In addition to proper collection and dispensing of biological fluids, such as breast milk or formula, it is also desirable to provide for the containment, mixing and delivery of pharmaceutical or nutritional supplements. Various consumer and/or professional applications would benefit from improved systems and methods for fluid collection and delivery.

It is to the provision of improved systems and methods for fluid collection and delivery that the present invention is primarily directed.

SUMMARY

In example embodiments, the present invention provides a container for collecting, storing and dispensing fluid. The container includes a hollow tube configured to receive a plunger.

In a first example, the present invention comprises a self-venting enteral syringe which includes a syringe body having an outside surface and defining a hollow internal cavity therein, the syringe body including an open end and a substantially closed end opposite the open end, the substantially closed end being integrally formed with the remainder of the syringe body. At least one vent extends from the hollow cavity to the outside surface of the syringe body and a plunger is operable to selectively travel within the hollow cavity. A port is positioned adjacent the substantially closed end.

In example forms, the vent is separate from the port and extends from generally adjacent the substantially closed end to outside the syringe body. Optionally, the vent can comprise two vents including a first vent separate from the port and extending from generally adjacent the substantially closed end to outside the syringe body and a second vent formed in the port. Also optionally, the port can comprise a double-lumen seal such that a supply/discharge lumen and vent lumen can be extended into the double-lumen port seal. In one example form, the vent is formed in or adjacent the port.

Optionally, a removable cap can be provided for covering and uncovering the substantially closed end of the syringe body. However, preferably the integrally-formed, substantially closed end functions as a non-removable cap.

Optionally, an offset tip is formed or located in the substantially closed end of the syringe body, the offset tip being positioned in a location offset from a center of the substantially closed end of the syringe body.

Advantageously, the vent(s) improve the filling of the syringe, while the integral cap provides a better, simpler closure at that end (and makes a separate cap/lid unneeded in most instances). The offset tip helps provide better control in the filling and dispensing and is particularly helpful in maintaining uniformity in dispensing from the syringe. The optional double-lumen port seal can provide convenient filling/dispensing, while also providing a useful vent. Also, by utilizing the optional female port, a male-to-male connection can improve safety.

In another example form, the present invention comprises a self-venting enteral syringe including a syringe body having an outside surface and defining a hollow internal cavity therein and at least one vent extending from the hollow cavity to the outside surface of the syringe body. The syringe body includes an open end and a substantially closed end opposite the open end, with the substantially closed end being integrally formed with the remainder of the syringe body. A plunger is operable to selectively travel within the hollow cavity, while a port is formed in or adjacent the substantially closed end. A vent is positioned in or adjacent the port.

In another example form the present invention is a luer-tip-restricting apparatus for use with liquid transfer equipment. The luer-tip-restricting apparatus includes a female port assembly with a hollow body and with a top opening edge, a bottom opening edge and a tapering inner diameter. The tapering inner diameter is designed to prevent formation of an air-tight fit with a luer tip. The luer-tip restricting apparatus also has at least one stop protruding from the tapering inner diameter. The at least one stop is positioned within the tapering inner diameter to prevent an air-tight fit with a luer tip inserted into the top opening edge of the female port assembly.

In another example form, the present invention is a cap for use with a syringe bottle having a conical lid, a female barrel-shaped port assembly and a generally continuous circumferential groove. The cap includes a top planar surface with an elliptical shape with a major axis and a minor axis. The major axis is longer than the minor axis. The cap includes a generally continuous collar extending from the edge of the top planar surface to a distal edge. The collar is constructed of resiliently flexible material. The cap includes a pair of opposing grips protruding inwardly from the generally continuous collar. The grips are configured to be removably inserted within the syringe bottle circumferential groove. The cap includes a plug that extends from the top planar surface within the generally continuous collar dimensions. The plug is designed to removably insert into the syringe bottle port assembly.

In another example form, the present invention is an adaptor for use with a syringe bottle having a conical lid, a female barrel-shaped port assembly and a generally continuous circumferential groove. The adaptor includes a resiliently flexible elliptical collar with a major axis and a minor axis. The adaptor includes a funnel with a sloping surface and an elongated port with a distal end. The funnel extends within the dimensions of the major axis and the minor axis. The adaptor includes a pair of opposing grips protruding inwardly from the elliptical collar and configured to be removably inserted within the syringe bottle circumferential groove.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 24A is a side view of the breast-pump adaptor of FIG. 23 as viewed along the minor Y axis.

FIG. 24B is a side view of the breast pump adaptor of FIG. 23 as viewed along the major X axis.

FIG. 25 is a perspective cross-sectional view of the breast pump adaptor of FIG. 23.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1D:
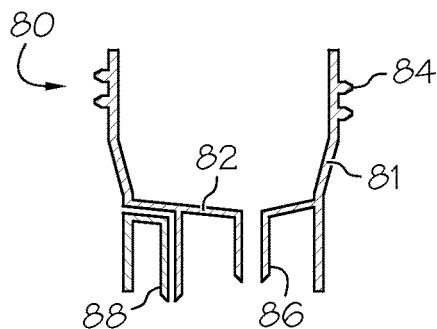
FIG. 1D is an accessory port assembly according to an example embodiment of the present invention.
Figure 1B:
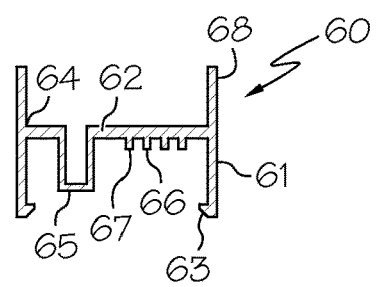
FIG. 1B is a sectional view of an optional removable cap portion of the syringe of FIG. 1A.

With reference now to the drawing figures, wherein like reference numbers represent corresponding parts throughout the several views, the drawing figures depict various embodiments of self-venting enteral syringes according to example embodiments of the present invention. FIG. 1A shows a self-venting enteral syringe 10 according to a first example embodiment of the present invention. In general, the enteral syringe 10 includes an elongated syringe body 20, a plunger 40, and an optional cover or cap 60.

Figure 1C:
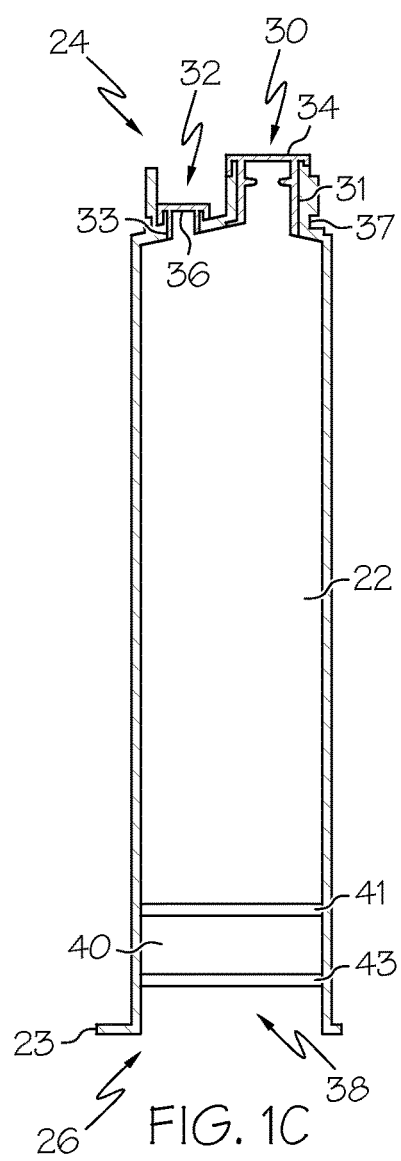
FIG. 1C is a sectional view of the self-venting enteral syringe of FIG. 1A.
Figure 1A:
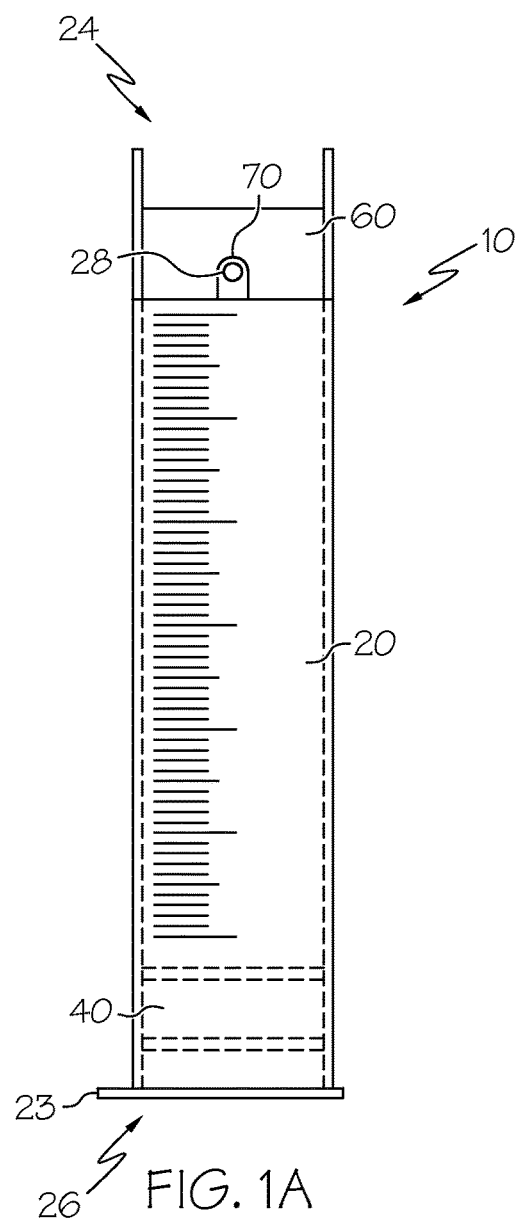
FIG. 1A is a side elevation view of a self-venting enteral syringe according to a first example embodiment of the present invention.

Referring now to FIG. 1C, the syringe body 20 defines an internal elongate cavity 22 that stretches substantially along the length of the body from an open end 26 towards a substantially closed end 24. In preferred example embodiments, the cavity 22 substantially matches the cross-section of the syringe body 20, providing a substantially constant outer-wall thickness of the same. The substantially closed end 24 comprises a supply/discharge port 30 and a vent 32, both integrally formed with the syringe body 20 and positioned generally adjacent the substantially closed end 24. The closed end 24 can also include an integrally formed mounting groove 37 for coupling with the cover or cap 60.

The supply/discharge port 30 extends from the internal cavity 22 to the outside surface of the syringe body 20 along a circumferential wall 31 and surrounds a port seal 34 mounted therein. The port seal 34 can be an integral flap, and integral fluid seal or a functional seal. Similarly to the supply/discharge port 30, the vent 32 extends from the internal cavity 22 to the outside surface of the syringe body 20 along a circumferential wall 33 and surrounds a vent port seal 36 positioned therein. Optionally, the supply/discharge port 30 and the vent 32 can be positioned in a position offset from the center of the substantially closed end of the syringe body 24. The optional offset position of port 30 and vent 32 can allow a more controlled filling and uniform dispensing of fluids.

The proximal end 26 of the syringe body 20 includes an opening 38 for receiving the plunger 40 therein and also includes a flange 23 for supporting the syringe in an upright position and assisting in use of the syringe. Optionally, the flange 23 can have an asymmetric cross section, for example to prevent the syringe 10 from rolling when lying in a non-vertical position. The syringe body 20 can have a substantially circular cross-section (as depicted in FIGS. 1-2), or can comprise an oval, elliptical, rectangular, or asymmetric cross-section as desired, and the opening 38 generally has a cross-section that is sized and shaped to snugly receive an inserted complementary plunger 40. The plunger 40 depicted in the figures comprises a first seal 41 and a second seal 43 to prevent fluid passage out of the contained volume 22, and allow the plunger to advance and retract within the syringe body 20. Optionally, the plunger can comprise one seal or may comprise two or more seals.

The cover or cap 60, as shown in FIG. 1B, is removably mountable to the substantially closed end 24 of the syringe body 20 and comprises a circumferential wall 61 extending from a circular lid panel 62 having a perimeter 64. A lower portion of the circumferential wall 61 comprises a partially circumferential mounting flange 63 for engaging the substantially closed end 24 of the syringe body 20, for example the mounting groove 37 shown in FIG. 1C. An upper portion of the circumferential wall 61 comprises a pinchable or squeezable rim 68 extending above the lid panel 62. The squeezable rim 68 can pivot about the perimeter 64 of the lid panel 62 to disengage the lower portion mounting flange 63 from the mounting groove 37, for example to remove the closure cap 60 from the syringe. Optionally, the closure cap can be attached to the body by a hinge or keeper, or can be non-removable, for example by entirely omitting the squeezable rim 68 or by having a fully circumferential rim. Additionally, the interior portion of the lid panel 62 comprises a sealing stem 65 and concentric ridges 66, 67, having an appearance much like a "bulls-eye" to provide a more positive seal with the port seal 34. With the closure cap coupled to the substantially closed end 24 of the syringe body 20, the stem 65 and ridges 66, 67 formed in the underside of the lid panel 62 are brought into sealing engagement with the top surface of port seal 34 and vent port seal 36 to provide a more positive seal against the elements.

To ensure a proper circumferential orientation of the interior sealing elements with respect to one another, the enteral syringe 10 can comprise an exposed notch 28 and the closure cap 60 can comprise a recessed portion 70. The notch 28 and the recessed portion 70 are engagable with each other and ensure proper orientation upon coupling the closure cap 60 to the syringe body 20. Additionally, the diameter of the circumferential wall 61 is substantially equivalent to the diameter of the syringe body 20.

Figure 10:
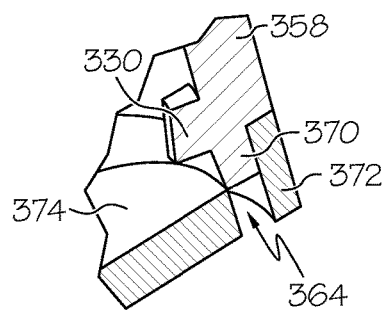
FIG. 10 is an enlarged sectional view of the view of FIG. 7.
Figure 11:
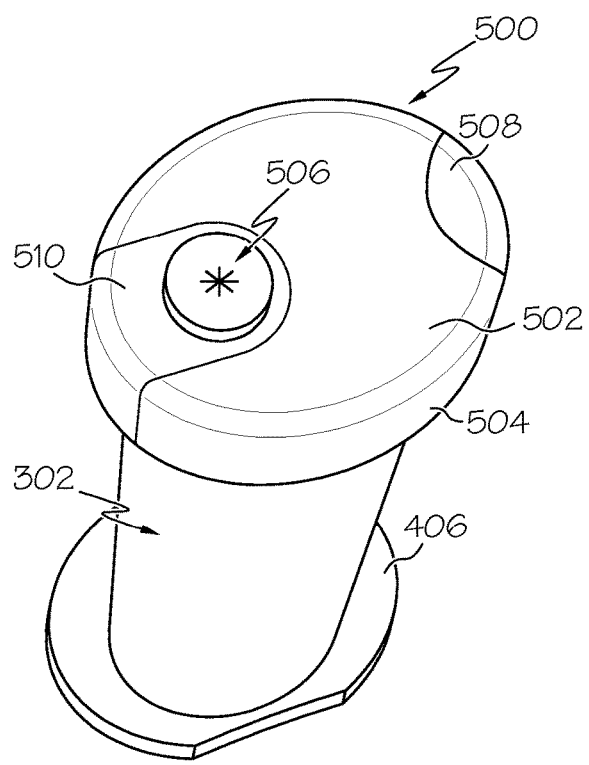
FIG. 11 is a perspective view of a cap secured to the luer-restricting syringe according to another example embodiment of the present invention.
Figure 12:
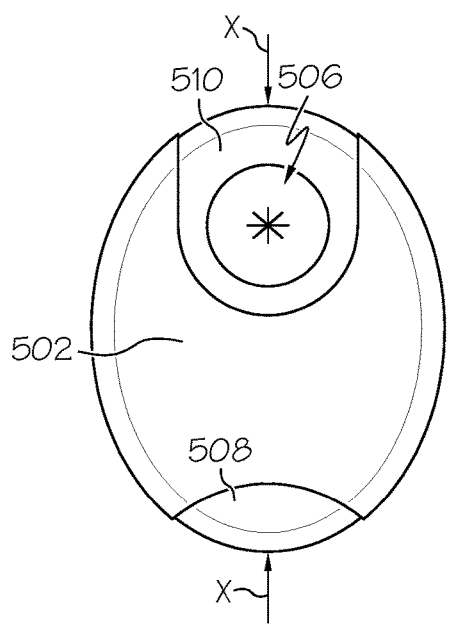
FIG. 12 is a top view of the cap of FIG. 11.
Figure 13:
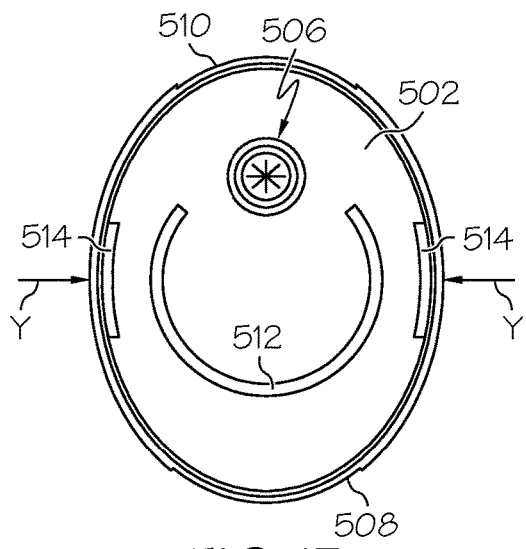
FIG. 13 is a bottom view of the cap of FIG. 11.
Figure 14:
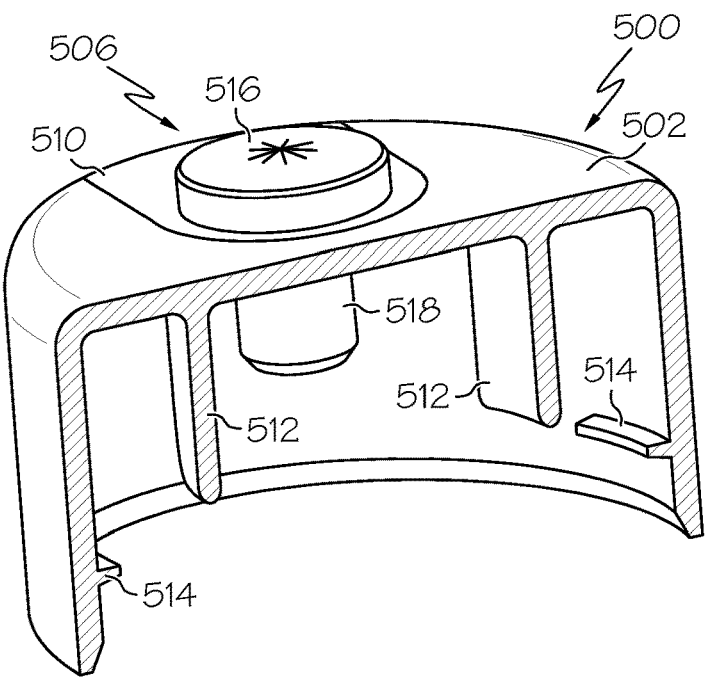
FIG. 14 is a perspective cut-away view of the cap of FIG. 11.

In additional example embodiments, FIG. 10 shows a breast pump attachment port assembly 80 for removably coupling to the substantially closed end 24 of the syringe body 20. The port assembly 80 comprises a circumferential wall 81 having a top portion with threading 84 on the exterior surface and a bottom portion surrounding a substantially closed shelf 82. The substantially closed shelf 82 comprises a fill/transfer nipple 86 for extending through the port seal 34 and a vent nipple 88 for extending through the vent port seal 36. The fill/transfer nipple 86 (can alternatively be termed a "straw," "port" or "spike") comprises an elongated cylindrical tube having a hollow interior portion extending through the shelf 82 to allow fluid communication with the interior of the cavity 22. The vent nipple 88 (can alternatively be termed a "straw," "port" or "spike") comprises an elongated cylindrical tube having a hollow interior portion extending along a path to the outside of the circumferential wall 81.

Figure 2B:
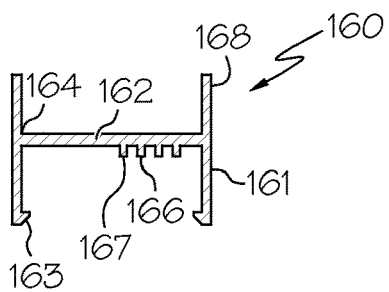
FIG. 2B is a sectional view of a removable cap according to another example embodiment of the present invention.
Figure 2D:
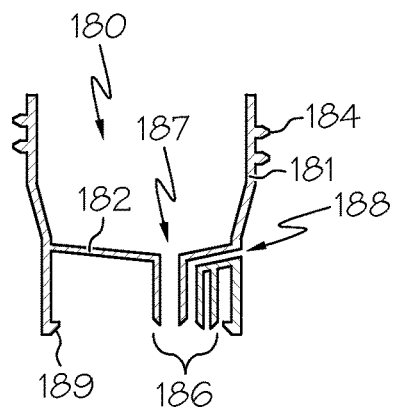
FIG. 2D is a sectional view of an accessory port assembly according to another example embodiment of the present invention.
Figure 2A:
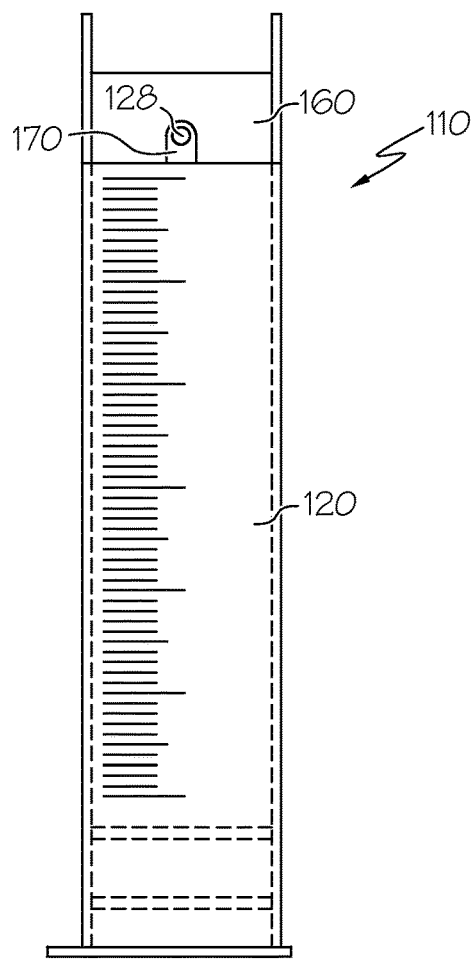
FIG. 2A is a side elevation view of a self-venting enteral syringe according to another example embodiment of the present invention.
Figure 2C:
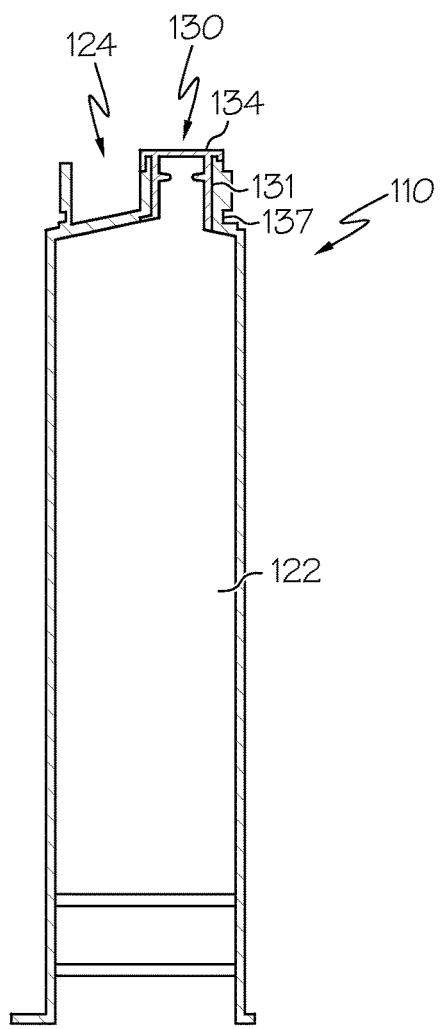
FIG. 2C is a sectional view of the self-venting enteral syringe of FIG. 2A.
Figure 2E:
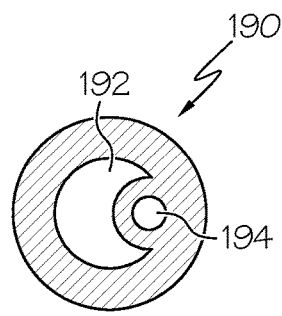
FIG. 2E is a plan view of a double-lumen seal portion of the self-venting syringe of FIG. 2A.
Figure 2F:
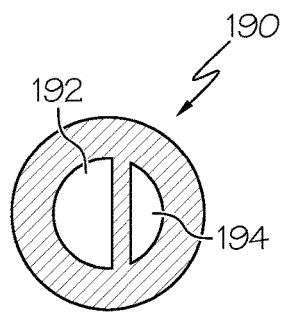
FIG. 2F is a plan view of an alternate version of a double-lumen seal according to another example embodiment of the present invention.
Figure 2G:
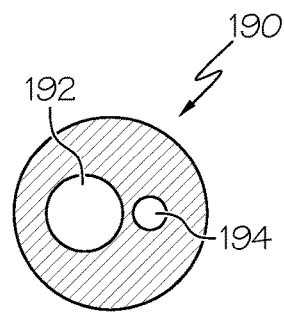
FIG. 2G is a plan view of yet a further double-lumen seal.
Figure 3:
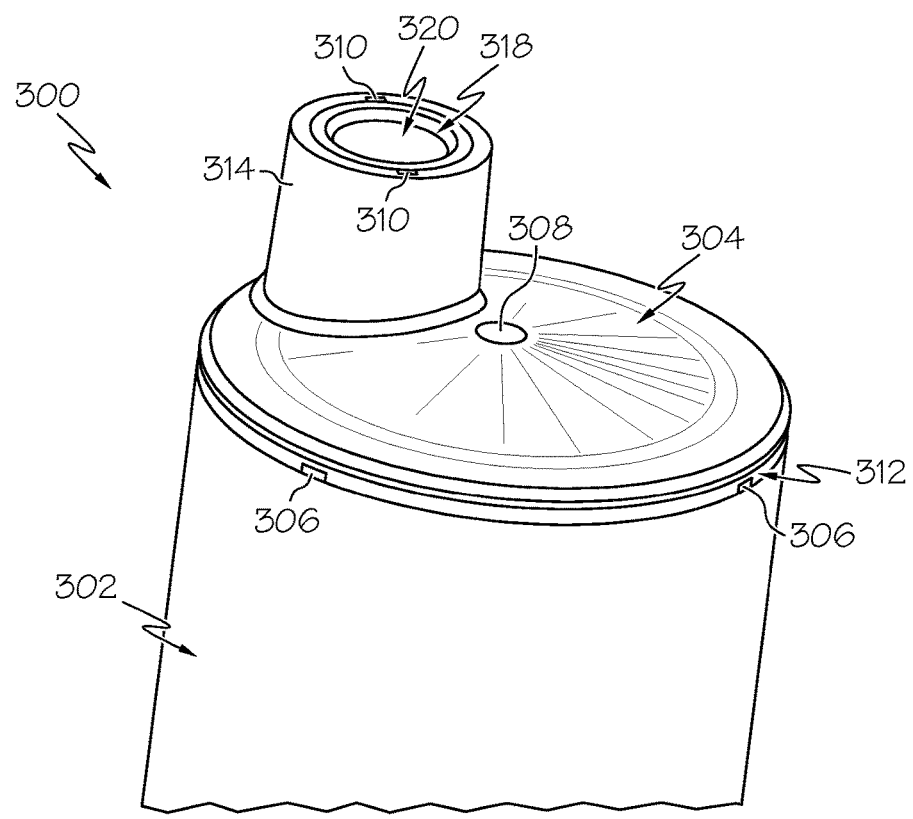
FIG. 3 is a first perspective view of a luer-restricting syringe according to another example embodiment of the present invention.
Figure 4:
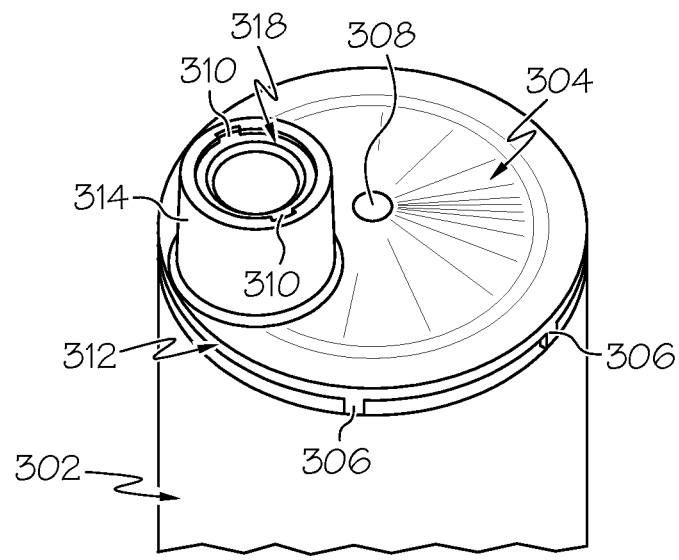
FIG. 4 is a second perspective view of the luer-restricting syringe of FIG. 3.

FIGS. 2A and 2C show an alternative embodiment of a self-venting enteral syringe 110, substantially similar to the above-described system 10 with differences as noted below. The syringe body 120 defines an internal elongate cavity 122 that stretches substantially along the length of the body from an open end 126 towards a substantially closed end 124. The substantially closed end 124 comprises a supply/discharge port 130 integrally formed with the syringe body 120 and extending generally adjacent the substantially closed end 124. The supply/discharge port 130 extends from the internal cavity 122 to the outside surface of the syringe body 120 along a circumferential wall 131 and surrounds a port seal 134. The port seal 134 is sealingly engaged within the circumferential wall 131 of the port 130 with a tight friction or interference fit and can comprise a double-lumen seal 190 (see FIGS. 2E-G). The double-lumen seal 190 comprises a supply/discharge lumen 192 and a vent lumen 194. The supply/discharge lumen 192 and the vent lumen 194 can have substantially circular cross-sections (as depicted in FIG. 2G), or can comprise an oval, elliptical, rectangular, or non-symmetrical cross-sections as desired (as depicted in FIGS. 2E-F).

The cover or cap 160, as shown in FIG. 2B, is removably mountable to the substantially closed end 124 of the syringe body 120 and comprises a circumferential wall 161 extending from a circular lid panel 162 having a perimeter 164. A lower portion of the circumferential wall 161 comprises a partially circumferential mounting flange 163 for engaging the substantially closed end 124 of the syringe body 120, for example the mounting groove 137 shown in FIG. 2C. An upper portion of the circumferential wall 161 comprises a pinchable or squeezable rim 168 extending above the lid panel 162. The squeezable rim 168 can pivot about the perimeter 164 of the lid panel 162 to disengage the lower portion mounting flange 163 from the mounting groove 137, for example to remove the closure cap 160 from the syringe. Optionally, the closure cap can be non-removable, for example by entirely omitting the squeezable rim 168 or by having a fully circumferential rim. Additionally, the interior portion of the lid panel 162 comprises concentric ridges 166, 167, having an appearance much like a "bulls-eye" to provide a more positive seal with the port seal 134. With the closure cap coupled to the substantially closed end 124 of the syringe body 120, the ridges 166, 167 formed in the underside of the lid panel 162 are brought into sealing engagement with the top surface of port seal 134 to provide a more positive seal against the elements.

To ensure a proper circumferential orientation of the interior sealing elements with respect to one another, the enteral syringe 110 can comprise an exposed notch 128 and the closure cap 160 can comprise a recessed portion 170. The notch 128 and the recessed portion 170 are engagable with each other and ensure proper orientation upon coupling the closure cap 160 to the syringe body 120. Additionally, the diameter of the circumferential wall 161 is substantially equivalent to the diameter of the syringe body 120.

FIG. 2D depicts a scaled alternative embodiment of a breast pump attachment port assembly 180. The port assembly 180 has a circumferential wall 181 having a top portion with threading 184 on the exterior surface and a bottom portion surrounding a substantially closed shelf 182 having a double-channel nipple 186 (can alternatively be termed a "straw," "port" or "spike"). The double-channel nipple 186 comprises a fill/transfer channel 187 and a vent channel 188. The fill/transfer channel 187 extends through the shelf 182 to allow fluid communication with the interior of the cavity 122 and is shaped to engage the supply/discharge lumen 192. The vent channel 188 extends along a path to the outside of the circumferential wall 181 and is shaped to engage the vent lumen 194. Additionally, the circumferential wall 181 has a partially circumferential mounting flange 188 for engaging the mounting groove 137 of the substantially closed end 124 of the syringe body 120.

In operation, the syringe 10, 110 of the present invention can be used in various applications, including the enteral administration of nutrients and/or medications to a patient. External devices, such as a breast pump, can be mounted to the port assembly by the threading. When the plunger is fully engaged into the cavity, fluid from the external device can be supplied to the syringe through the fill/transfer nipple or the fill/transfer channel of the double-channel nipple. As fluid begins to fill the cavity, excess air or gas within the cavity can be removed by the vent nipple, the vent channel, or a combination of both. Additionally, a male-to-male adaptor tube can be formed. The male-to-male adaptor tube can accommodate enteral feeding by connecting the female port of the self-venting enteral syringe to a traditional female extension of an enteral feeding tube.

All of the components discussed and described herein can be formed from plastics (i.e. polypropylene), other polymers, glass, metals, metal alloys, resins, rubbers, rubber derivatives, elastomerics (i.e. santoprene), silicones or other known materials. In example embodiments, the syringe body 20, 120 can be formed from polypropylene, polyethylene or polypropylene copolymers, the plunger is formed from the same, and the plunger seals formed from elastomer 40, 140 is formed from an elastomeric. Optionally, color additives may be added to provide protection from UV light and/or colorants may be added to the syringe 10, 110 as desired and/or to identify certain properties/characteristics (i.e. administration path) or contents. In alternative embodiments, the syringe can include external markings to indicate volume capacity and remaining content levels.

An alternative embodiment enteral-only luer-restricting syringe is described in FIGS. 3-10. The luer-restricting syringe allows a single syringe body to receive, store, transport, transfer and deliver fluid within a single chamber. A lid 304 is secured to an open end of a cylindrical syringe body 302 through a variety of methods, including friction fit, corresponding threading, tongue and groove, or adhesive. Preferably, the lid 302 is integrally co-molded with the syringe body 302. Similarly to the syringe bodies 20, 120 described above, the alternative syringe body 302 defines an elongate interior cavity chamber for receiving and storing material, for example fluid. The syringe body 305 has a generally circular circumference. A generally continuous groove 312 is extends around the outer circumference between the lid 304 and the syringe body 302. The continuous groove 312 can be integrally formed with the syringe body 302. Alternatively, a continuous groove can be formed around the outer surfaces of either the lid or the syringe body. As depicted, the groove 312 includes a pair of ribs 306 that interrupt the continuity of the groove. Additional ribs 306 can alternatively be included within the groove 312. The ribs 306 act as barriers to prevent unwanted rotation of adaptors or caps with respect to the groove 312, as described further below. As depicted, the lid 304 can be generally conical with a peak 308 and a hollow interior. However, alternative shapes can be similarly effective.

As depicted, a female supply/discharge port assembly 300, including a barrel receiver 314 and chimney insert 318, extends upwardly over an aperture (not shown) in the lid 304. The supply/discharge port assembly 300 can be secured to the lid through a variety of fixation methods, including friction fit, corresponding threading, tongue and groove, or adhesive. Preferably, the barrel receiver 314 can be integrally co-molded with the lid 304. The chimney insert 318 is separably secured within the barrel receiver 314. The chimney insert 318 can be secured with respect to the barrel receiver 314 through an interference or friction fit, conjoined through adhesives, bonded through heat, radiofrequency, ultrasonic, or over-molded by molding the barrel receiver over the chimney insert. As further depicted in FIGS. 5A-5C, an integral continuous groove 380 extends around the circumferential interior surface of the barrel receiver 314. As depicted, the barrel receiver 314 can include a pair of opposing wing recessions 310 defined longitudinally-parallel along the interior surface of the barrel receiver 314 from the top edge to a defined termination position before reaching the continuous groove 380. Alternatively, the barrel receiver 314 can include a greater or lesser number of wing recessions 310 positioned at various locations on the internal circumference. As depicted, the barrel receiver 314 has a circumferential surface with variable height at particular locations between the top and bottom openings along the circumference, thus producing a slanted bottom edge with a minimum and maximum height.

As depicted, the chimney insert 318 includes an upper region 354, a lower region 358 and a neck 370. The chimney insert 318 is preferably integrally molded as a continuous unitary body and can be constructed of a rigid, durable material, for example plastic or metal. The chimney insert 318 has an inner passageway 320 with a generally consistent diameter. The upper region 354 includes a top edge and transition surface 352 leading into the inner passageway 320. The upper region 354 can also include a pair of opposing wing protrusions 350 having a substantially similar shape and dimensions as the barrel receiver wing recessions 310. The protrusions 350 are designed to be securely received within the wing recessions 310 in the barrel receiver 314. A continuous ridge 356 protrudes around the circumferential outer surface of the chimney insert 318 and distinguishes the upper region 354 from the lower region 358. The continuous ridge 356 is designed to secure within the continuous groove 380 in the barrel receiver 314. As depicted, the upper region 354 and the lower region 358 can have a generally consistent outer diameter.

The neck 370 extends from below the lower region 358. The neck 370 has a smaller outer diameter than the upper 354 and lower 358 region outer diameters, thus producing an overhang of the lower region over the neck. A finger protrusion 333 extends onto the outer surface of the neck 370. The finger protrusion 333 has an outer-surface diameter consistent with the lower region 358, thus creating a generally consistent outer surface across the lower region and the finger protrusion. The finger protrusion 333 is designed to be received in a finger recession 378 of a seal, as further described below. As depicted, the neck 370 has a circumferential surface with variable height at particular locations along the circumference between the top and bottom openings, thus producing a slanted bottom edge with a minimum and maximum height.

A pair of stops 330 protrude from the interior surface of the chimney insert 318. As depicted, the stops 330 are positioned opposite each other along inner surface of the lower region 358 of the chimney insert 318. Alternatively, a single stop or multiple stops can extend from the inner surface of the chimney insert 318. As depicted, the stops 330 can have a tapered inwardly-facing surface that narrows in diameter toward the neck 370. Alternatively, the inwardly-facing surface of the stops 330 can have a consistent diameter.

Figure 5A:
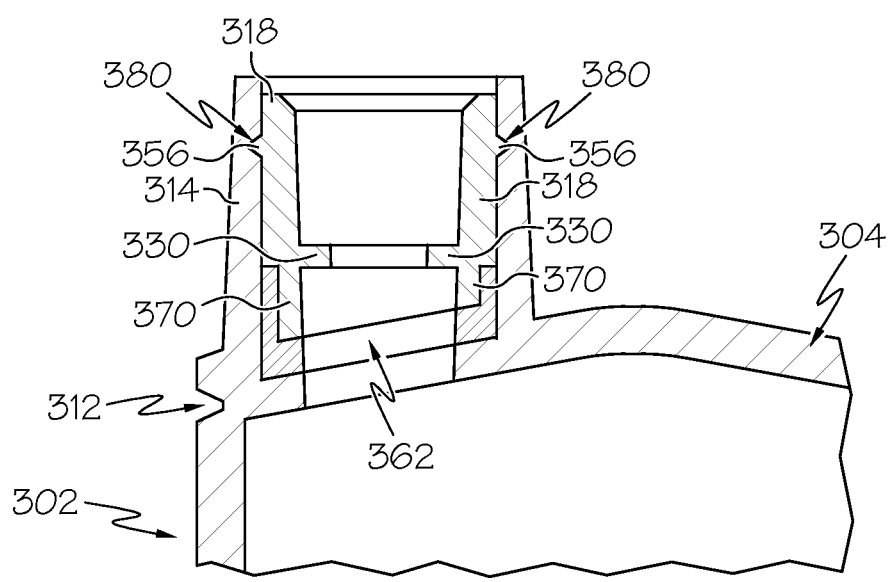
FIG. 5A is a cross-sectional view of the luer-restricting syringe of FIG. 3.
Figure 5B:
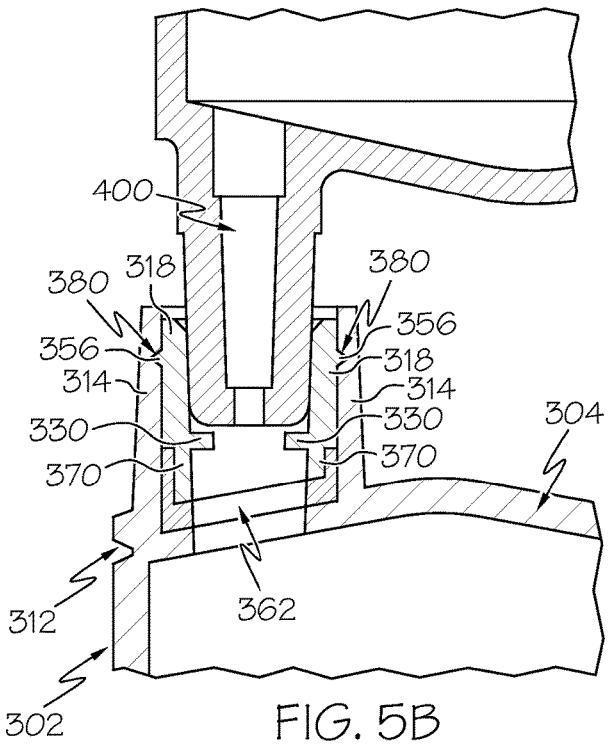
FIG. 5B is a cross-sectional view of the luer-restricting syringe of FIG. 3 in use with an enter-only syringe.

The chimney insert 314 has a tapering inner diameter that is designed to receive an enteral-only syringe tip 400, such as shown in FIG. 5B. A commercially-available enteral-only syringe tip 400 has a tapered shape. The inner diameter of the chimney insert 314 has a larger upper diameter and a smaller lower diameter in order to correspond with a commercial enteral-only tip. Upon being inserted into the top opening of the passageway 320 of the chimney insert 314, the tapered enteral-only tip 400 creates a friction-fit air-tight seal with the chimney at the point when the tapered enteral-only tip 400 diameter matches the chimney insert 314 diameter. As shown, the friction-fit air-tight seal is formed without the enteral-only tip 400 contacting the stops 330. This friction-fit air-tight seal allows fluids to be transferred between the enteral-only syringe 400 and the syringe body 302 without acquiring outside contaminants.

Figure 5C:
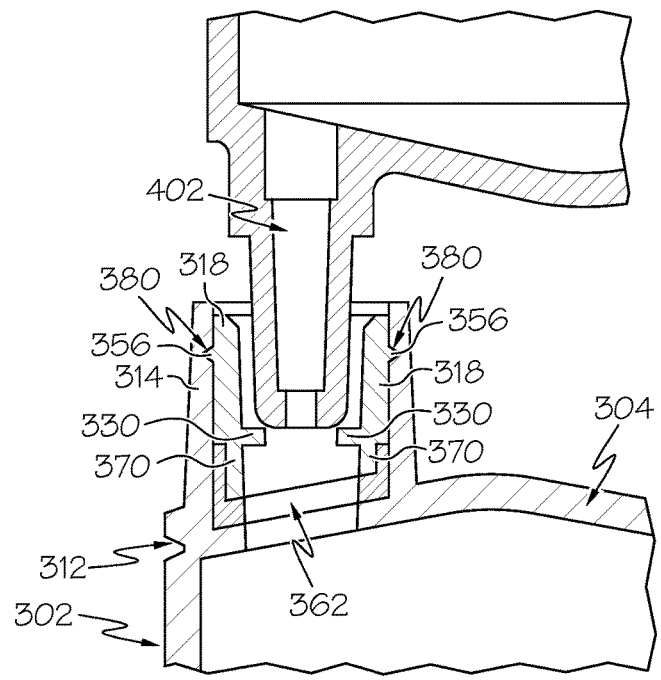
FIG. 5C is a cross-sectional view of the luer-restricting syringe of FIG. 3 in use with a luer slip tip.
Figure 6:
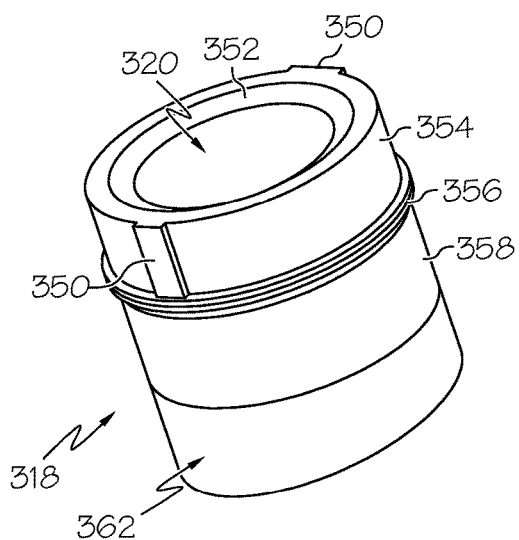
FIG. 6 is a perspective view of a chimney insert and seal attachment used with the luer-restricting syringe of FIG. 3.
Figure 7:
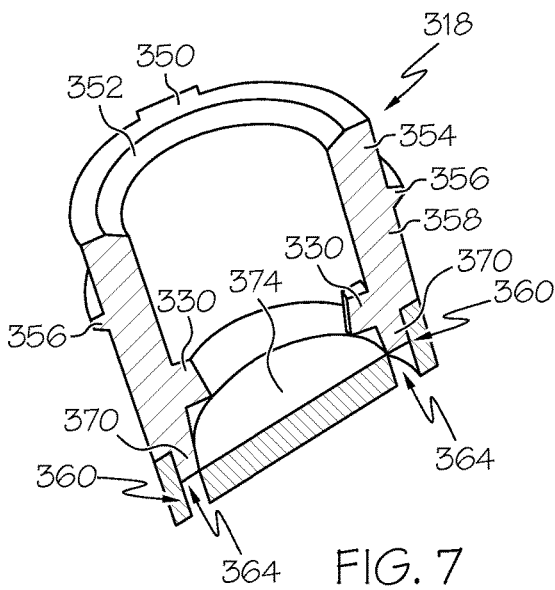
FIG. 7 is a perspective cross-sectional view of the chimney insert and seal attachment of FIG. 6.
Figure 8:
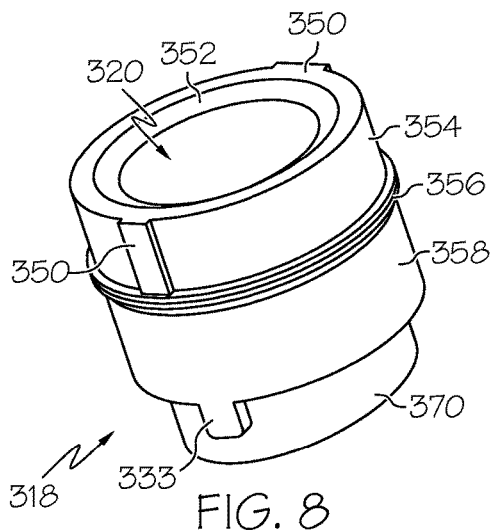
FIG. 8 is a perspective view of the chimney insert of FIG. 6 without the seal attachment.
Figure 9:
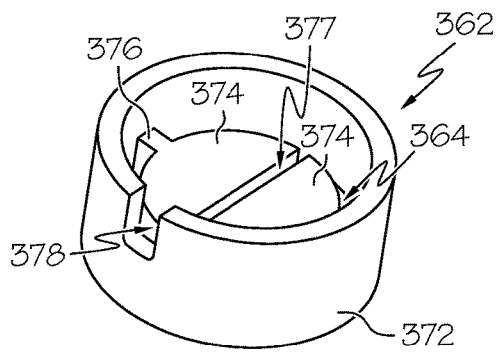
FIG. 9 is a perspective view of the seal attachment of FIG. 6 removed from the chimney insert.

As depicted in FIG. 5C, the chimney insert 314 is designed to not create an air-tight seal with a commercially-available luer tip 402, for example a luer-slip-tip, having dimensions defined by ISO 594/1-1986(E) and ISO 594-2: 1998(E) conical fittings with a 6% Luer taper for syringes, needles and certain other medical equipment, hereby incorporated by reference for all purposes. A commercially-available luer tip 402, or luer-slip-tip has a smaller minimum diameter and smaller maximum diameter than the enteral-only tip 400. As depicted, the stops 330 prevent the luer tip 402 from extending within the chimney insert 314 to a distance that would be required for the luer tip 402 to form an air-tight friction-fit with the chimney insert. Specifically the distance between the stops 330, specifically the inwardly-facing surface has a maximum of, or is preferably less than, 3.925 mm, which is the minimum diameter for a 6% Luer tip end of the male conical fitting as defined by ISO standards. Additionally, the diameter of the top opening of the chimney insert 318 has a minimum of, or is preferably greater than, 4.315 mm, which is the maximum diameter at the opening of a female conical fitting to receive a 6% luer conical fitting. This inability to form a friction-fit air-tight seal prevents the chimney insert 314 from being effectively used with a luer tip 402 because contaminants cannot be excluded from any liquid being transferred between the luer tip and the syringe body 302. This meets the provisions of such standards as ISO 80369 by restricting engagement of luer connectors and enteral connectors to prevent intermingling of the fluid paths.

A seal attachment 362 is depicted to attach with respect to the neck 370 of the chimney insert 318. The seal attachment 372 has a continuous circumferential collar 372 that fits around the neck 370 and has an outer diameter that is generally consistent with the outer diameter of the lower region 358 of the chimney insert 318. The continuous circumferential collar 372 also has a finger cutout 378 to receive the finger protrusion 333 on the chimney insert 318.

The continuous circumferential collar 372 is secured around the neck 370 through a friction-fit and/or an adhesive. The seal attachment 372 includes a pair of flaps 374. As depicted, the flaps 374 have a generally semi-circular shape with a smaller diameter than the interior diameter of the continuous circumferential collar 372, thus providing a generally-continuous gap 364 between the flaps and the continuous circumferential collar. The flexible flaps 374 are secured to the continuous circumferential collar 372 through a pair of bridge mounts 376. As depicted, the flaps 374 are separated by an elongated channel 377. The seal 362 is preferably constructed as a single unitary body including the continuous circumferential collar 372, the bridge mounts 376 and the flaps 374. The seal attachment 362 is preferably constructed of a flexible material, for example plastic, rubber or silicone.

In use, the seal attachment 372 is secured with respect to the chimney insert neck 372 and the flaps 374 prevent or restrict solid particles from entering or exiting the syringe body 302 and to augment the flow of fluid into and out of the syringe body. Alternatively, the flaps 374 can be secured directly to the circumferential collar 372 without the gap 364. Alternatively still, the flaps 374 can resiliently rest together forming an air-tight seal that is only broken with a protruding body, for example a tube or straw, that is forced between the flaps.

As depicted in FIGS. 11-22, the syringe body 302 can be stored or transported standing vertically upright on a platform 406. In storage or transport, the contents held within the internal chamber of syringe body 302 can be protected with a removable cap 500.

The cap 500 has a top planar surface 502 and a generally continuous collar 504 extending downwardly from the edge of the top planar surface. The collar 504 can have a consistent height from the top planar surface 502 to a distal edge. The generally continuous collar 504 is preferably constructed of resiliently-flexible material, for example plastic. As depicted, the top planar surface 502 can have an elliptical shape with a major (X) axis and a minor (Y) axis. A first pinch recession 508 can be formed at one end of the major (X) axis. A second pinch recession 510 can be formed at an opposite end of the major (X) axis. The first 508 and second pinch recessions 510 can extend partially along the top planar surface 502 and generally across the height of the collar 504. In use, inwardly-directed pinching pressure applied simultaneously to the first 508 and second 510 pinch recessions, along the major (X) axis, causes the resiliently-flexible collar 504 to change its shape to shorten the major (X) axis and lengthen the minor (Y) axis. When this simultaneous pressure is released, the resiliently-flexible collar 504 returns to the pre-pressure relaxed state.

A pair of teeth grips 514 extend inwardly from the interior surface of the collar 504. As depicted, the teeth grips 514 can be positioned diametrically opposite each other, and separated by and along the minor (Y) axis. Alternatively, additional pairs of teeth grips at alternative locations can be similarly effective. The teeth grips 514 are preferably integrally co-molded with the cap 500. The teeth grips 514 have a shape that is designed to removably insert into the continuous groove 312 between the lid 304 and the syringe body 302 described above. In a relaxed state without application of a pinching pressure described above, the minor (Y) axis length is shorter than the diameter of the syringe body 302. In a similarly relaxed state, the minor (Y) axis length is generally equivalent to the distance between opposing points along the inner-most surface of the continuous groove 312. In the relaxed state, the resilient force of the cap 500 presses the teeth grips 514 into the continuous groove 312, thus preventing the cap from involuntary removal during transport or storage. Correspondingly to that described above, applying a simultaneous major (X) axis pinching pressure to each pinch recession 508, 510 elongates the minor (Y) axis and removes the teeth grips 514 out of the continuous groove 312 so that the cap 500 can be removed. In use a depicted in FIG. 17, the teeth grips 514 preferably insert into the continuous groove 312 between the pair of ribs 306 to prevent the cap 500 from rotating with respect to the groove.

Figure 15A:
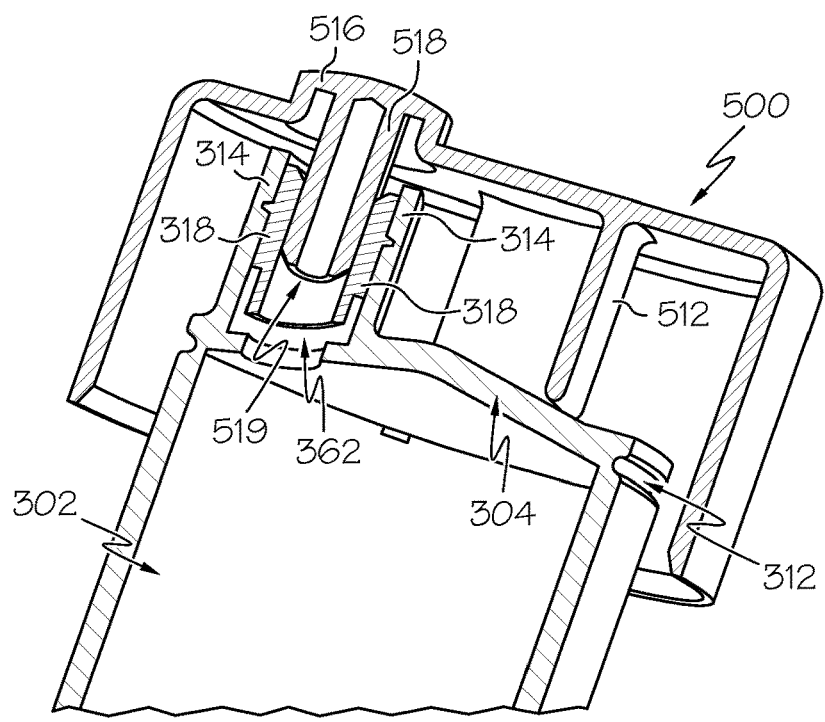
FIG. 15A is a perspective cross-sectional view of the cap of FIG. 11 secured to the luer-restricting syringe of FIG. 3.
Figure 15B:
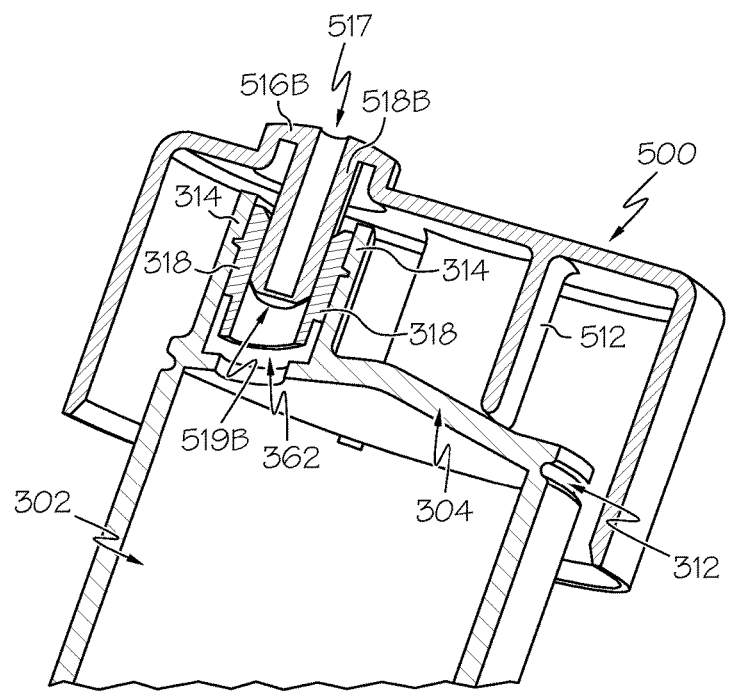
FIG. 15B is a perspective cross-sectional view of an alternative example embodiment of the cap of FIG. 11 secured to the luer-restricting syringe of FIG. 3.

As depicted, a plug is secured through an aperture (not shown) in the top surface region of the second pinch recession 510. The plug includes a base that secures above the top surface 502 and a rigid probe that extends through the aperture (not shown) and below the top surface. The plug is preferably integrally constructed of a unitary single-body construction. The probe preferably is tapered and has dimensions that are generally consistent with an enteral-only tip, similar to the tip 400 described above. A first example plug 506 can have an opening in the distal end 519 of the probe 518 with a hollow bore extending to a closed base 516. Alternatively as shown in FIG. 15B, a second example plug can have a base 516B with an opening 517 and a bore that extends into a probe 518B that has a closed distal end 519B. Alternatively still, a third example plug can have a solid base and solid probe without any openings or internal bores.

The plug can be separately constructed and then fixed through the cap 500 through a variety of fixation methods, including friction fit, threading, and adhesive. Preferably, the plug can be integrally co-molded with the cap 500 to form a unitary body.

In use, the probe 518, 518B inserts into the passageway 320 in the above-described chimney insert 318 until it forms an air-tight friction-fit seal similar to that described with the enteral-only tip 400. This seal is air-tight and prevents unwanted material from entering or exiting the syringe body 302 during storage or transport.

Figure 16:
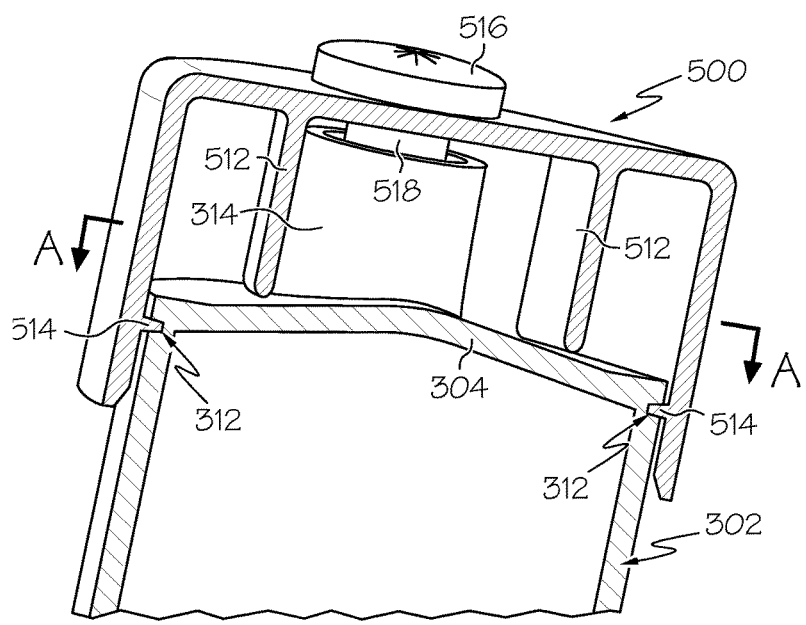
FIG. 16 is a perspective cut-away view of the cap of FIG. 11 secured to the luer-restricting syringe of FIG. 3.
Figure 17:
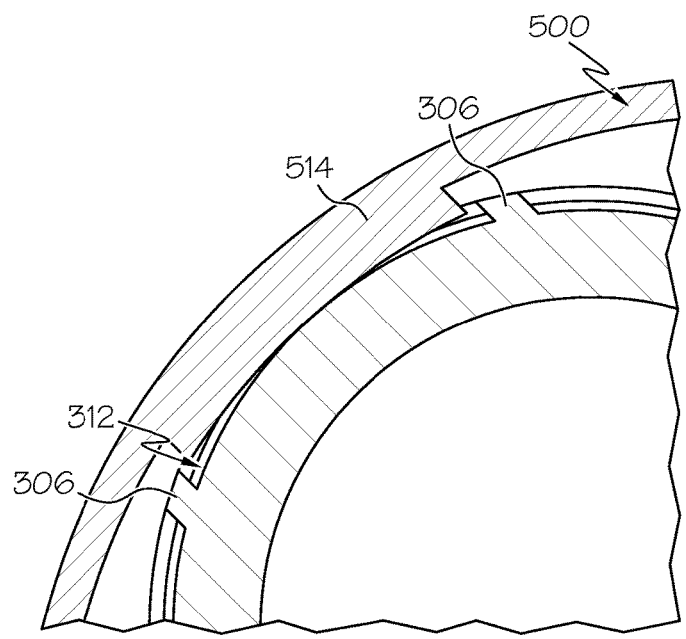
FIG. 17 is a cross-sectional view of the cap of FIG. 11 secured to the luer-restricting syringe of FIG. 3 as viewed along line A in FIG. 16.
Figure 18:
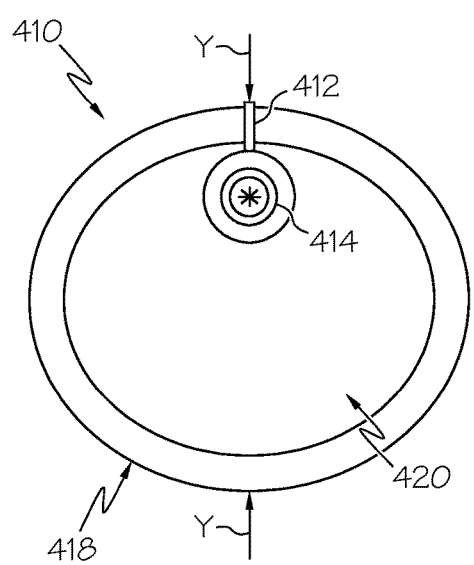
FIG. 18 is a top view of an alternative example embodiment of the cap of FIG. 12 according to another example embodiment of the present invention.
Figure 19:
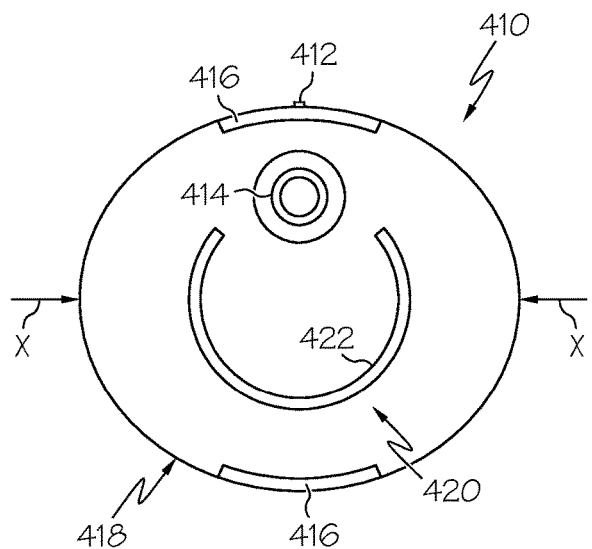
FIG. 19 is a bottom view of the cap of FIG. 18.
Figure 20:
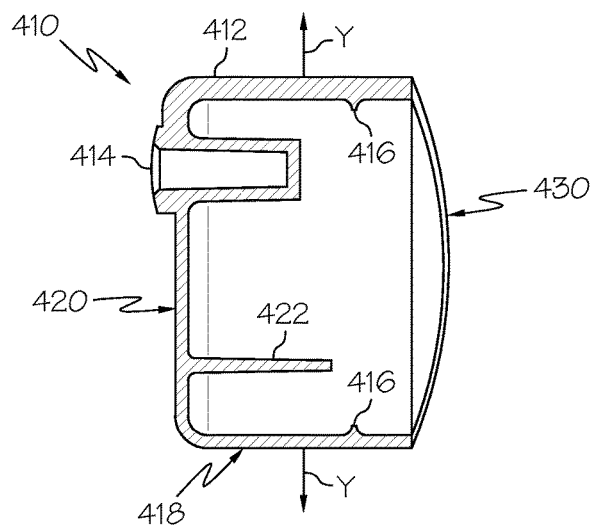
FIG. 20 is a cross-sectional side view of the cap of FIG. 18 as viewed along the major X axis.
Figure 21:
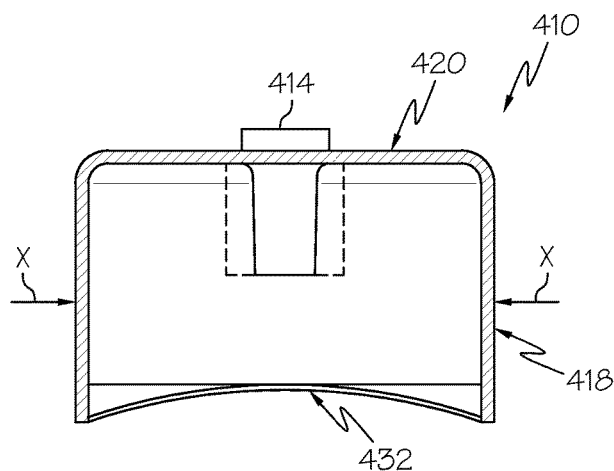
FIG. 21 is a cross-sectional view of the cap of FIG. 18 as viewed along the minor axis.
Figure 22:
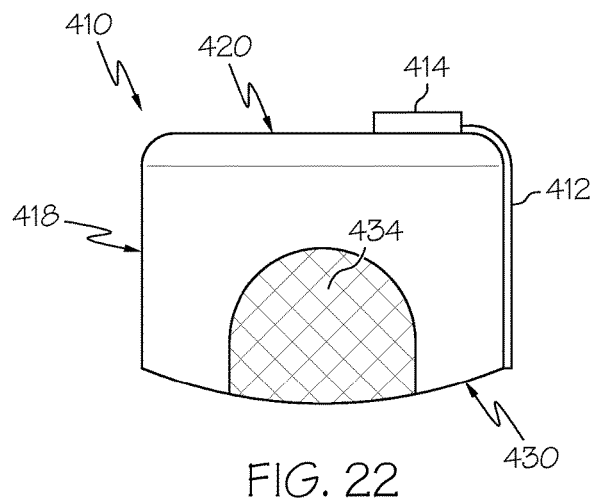
FIG. 22 is a side view of the cap of FIG. 18 as viewed along the major X axis.

A rigid support 512 extends downwardly from the top planar surface 502 within the cap 500. As depicted, the support 512 can have a semi-circular wall shape with a disconnect. As further depicted, the support 512 can be positioned with respect to the cap 500 such that the plug 506 is positioned within the disconnect of the semi-circular wall shape. As depicted, the plug 506 and support 512 can be aligned offset from center along the major (X) axis. In use, when the probe 518, 518B is inserted into the chimney insert 318, a distal edge of the support 512 contacts the lid 304. This contact between the support 512 and the lid 304 assists to prevent the probe 518, 518B from inserting an unwanted distance into the chimney 314, as shown in FIGS. 15A-16. The semi-circular shape of the support 512 corresponds with the cone shape of the lid 304 to maintain an even distribution of support. The proximal end of the support 512 can be fixed to the cap 500 through a variety of fixation methods, including friction-fit and adhesive. Preferably, the support 512 is integrally co-molded with the cap 500 to form a unitary structure.

As depicted in FIGS. 18-22, an alternative cap 500A can align a plug 414 and support 422, of similar design and structure to plug 506 and support 512 described above, along the center of the minor (Y) axis, thus turned ninety degrees and shifted toward center from the cap 500 described above. Similarly to the cap 500 described above, a pair of teeth grips 416 are depicted to align along and be separated by, the minor (Y) axis.

Figure 23:
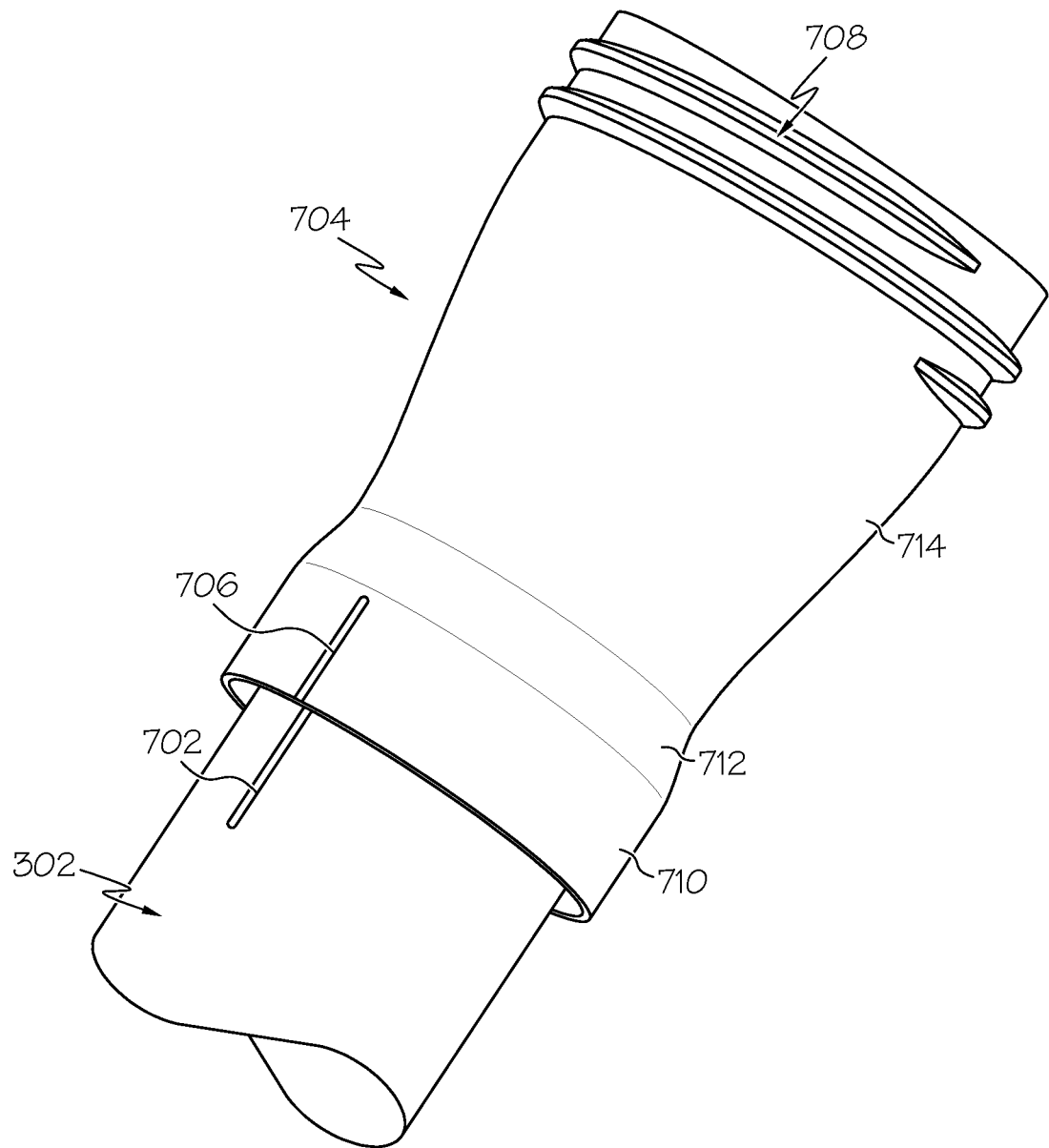
FIG. 23 is a perspective view of a breast-pump adaptor according to another example embodiment of the present invention, shown secured to the syringe body of FIG. 3.

An elongated marker 412 can integrally protrude from the outer surface of the cap 500A and extends from the plug downwardly along the outside of the collar 418. This marker 412 assists a user to align the cap 500A with a marker 702 on the syringe body 302 described below in FIG. 23. The marker 412 can alternatively be a recessed groove or surface indicator. A similar marker can be integrated with cap 500.

As depicted, the collar 418 can have a variable height from the top planar surface to the distal edge. As viewed along the major (X) axis in FIG. 22, the distal edge can have a pair of opposing convex outward arcs 430. As viewed along the minor (Y) axis in FIG. 21, the distal edge can have a pair of concave inward arcs 432. There can be a smooth transition between the convex 430 and concave 432 arcs. A pinch grip 434 having a textured criss-crossed or embossed pattern, or similar surface, is depicted to be present on a side of the cap so as to improve usability. As depicted, the pinch grip 434 can be located on the outer surface along the major (X) axis of the cap. Alternatively, the collar 418 can have a pair of opposing pinch grips on either end of the major (X) axis.

FIGS. 23-28 shows an adaptor 704 that can attach to the enteral-only syringe described above. As depicted, the adaptor 704 has a base region 710, a mouth region 714 and a transition waist 712 between the base and the mouth. There is an opening 720 through the mouth 714 and an opening 730 through the base 710. As depicted, the mouth region 714 and waist region 712 have a generally circular circumference. The waist 712 is depicted to have a smaller diameter than the mouth 714. The mouth 714 can include an attachment mechanism 708, for example a threaded outer surface, to attach a standard commercially-available breast pump.

As depicted in FIGS. 24A and 24B, the base region 710 can have an elliptical shape similar to the cap collars 504, 418 described above. FIG. 24A shows the base region 710, as viewed along the minor (Y) axis and FIG. 24B shows the base region as viewed along the major (X) axis. Similarly to the cap collars 504, 418 described above, the base region 710 is preferably constructed of resiliently-flexible material, for example plastic. In use, pinching pressure applied simultaneously to the opposing ends of the base region 710, along the major (X) axis, causes the resiliently-flexible base 710 region to change its shape to shorten the major (X) axis and lengthen the minor (Y) axis. When this simultaneous pressure is released, the resiliently-flexible base region 710 returns to the pre-pressure relaxed state and dimensions.

As depicted, the base region 710 can include a pinch grip 711 on one of the opposing ends of the major (X) axis to improve usability when applying pinch pressure. Alternatively, the base region 710 can have a pair of opposing pinch grips on either end of the major (X) axis. The pinch grip 711 can have a criss-crossed, embossed or similar textured appearance.

A funnel 723 separates, and enables fluid passage between, the interior of the mouth region 714 from the interior of the base region 710. The funnel 723 includes a generally-circumferential slide 738 that directs any liquid or material downward towards a port 732. The port 732 is depicted to be hollow and elongated and has a distal end that extends within the base region 710 of the adaptor 704. The slide 738 extends from the inner wall of the adaptor 704 and includes a downwardly-sloped surface. The downwardly-sloped surface extends towards the port 732. The port 732 is preferably positioned off-center and toward an end of the major (X) axis, preferably near the waist 712.

Figure 26:
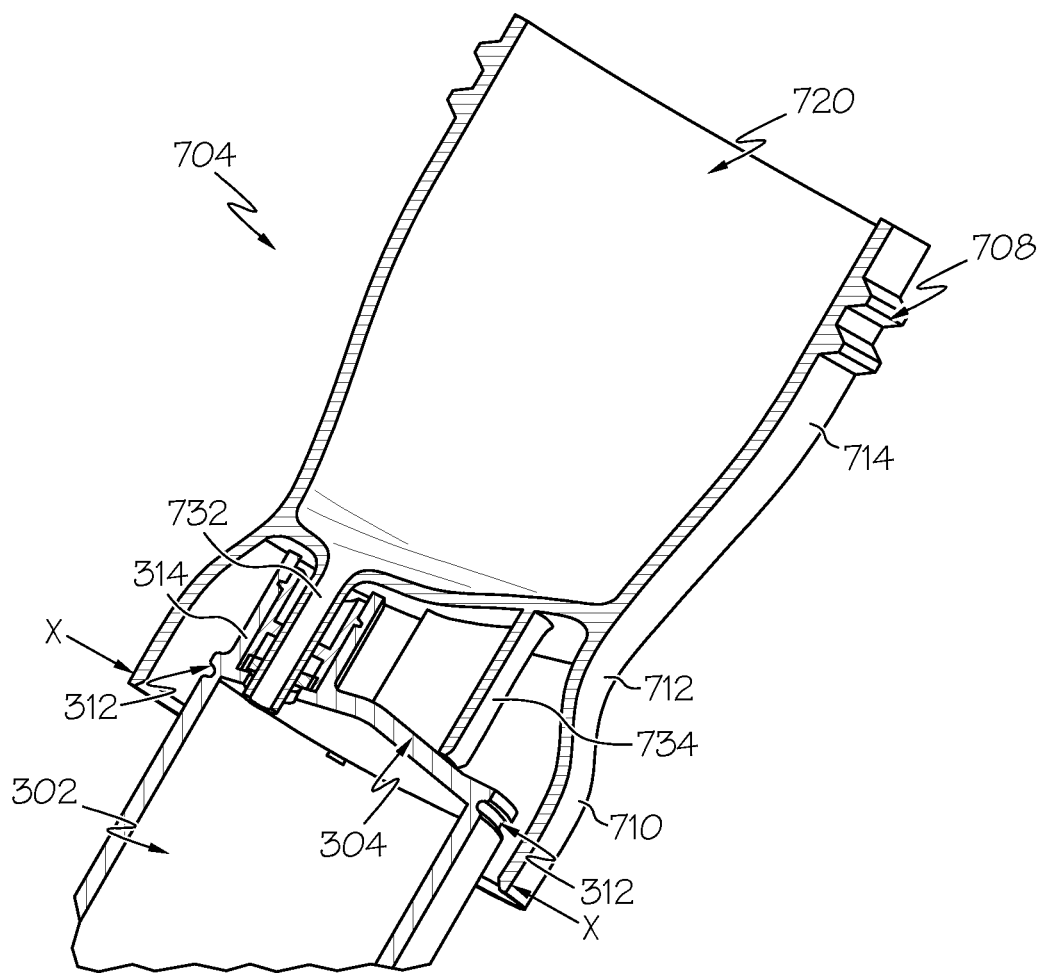
FIG. 26 is a perspective cross-sectional view of the breast-pump adaptor of FIG. 23 secured to the syringe body of FIG. 3.

A support 734 extends downwardly away from the slide 738. The support 734 can have a semi-circular wall shape with disconnect similar to the supports 512, 422 in the caps 500, 410 described above. The support 734 can also be positioned such that the port 732 is situated within the disconnect of the semi-circular wall shape. In use, the port 732 is inserted into the passageway 329 of the chimney 318 in the lid 304. The port 732 has a narrow diameter preventing the port from creating a, air-tight seal with the chimney insert 318. The port 732 has a length that allows it to extend through the channel 377 between the flaps 374 in the seal without forming an air-tight seal. This allows easy introduction of liquid into the syringe body 302 with simultaneous venting of any trapped air within the syringe body chamber. A distal end of the support 734 contacts the lid 304 without applying any pressure to the lid. This alignment of the support 734 and the lid 304 assists to prevent the port 732 from inserting an unwanted distance into the chimney 314, as shown in FIG. 26. The semi-circular shape of the support 732 corresponds with the cone shape of the lid 304 to maintain an even distribution of support.

Similarly to the alternative cap 500A described above, the position of the port, funnel and support in the adaptor 704 can be turned ninety degrees and centered to aligned along the minor (Y) axis.

Similarly to the caps 500, 410 described above, the adaptor 700 can include a pair of similarly-designed teeth grips 736 that extend inwardly from the interior surface of the base region 710. The teeth grips 736 can extend from diametrically opposed locations along the major (X) axis of the base region 710. Alternatively, additional teeth grips 736 at alternative locations can be effective. The teeth grips 736 are preferably co-molded with the adaptor 704. The shape of the teeth grips 736 is designed to removably insert into the circumferential groove 312 between the lid 304 and the syringe body 302. The resilient force of the base region 710 presses the teeth grips 736 into the circumferential groove 312 when the base region is in a relaxed state, thus preventing the adaptor 704 from involuntary removal during use. Applying simultaneous inward pinching pressure to opposing ends of the base 710 major (X) axis elongates the minor (Y) axis and removes the teeth grips 736 out of the circumferential groove 312 so that the adaptor 704 can be removed. Similarly to the caps 500, 410 described above, the teeth grips 736 preferably insert between the pair of ribs 306 in the groove 312 to prevent the adaptor 704 from rotating within the groove.

The syringe body 302 can alternatively have a marker 706 that aligns with a corresponding marker 706 on the adaptor 704 when the adaptor is secured to the syringe body. As depicted in FIG. 26, the markers 702, 706 can be elongated etchings on the exterior surface of the syringe body 302 and adaptor 704, however, alternative shapes are considered effective. The markers 702, 706 can alternatively be bodies protruding from the outer surface or surface indicators.

Figure 27:
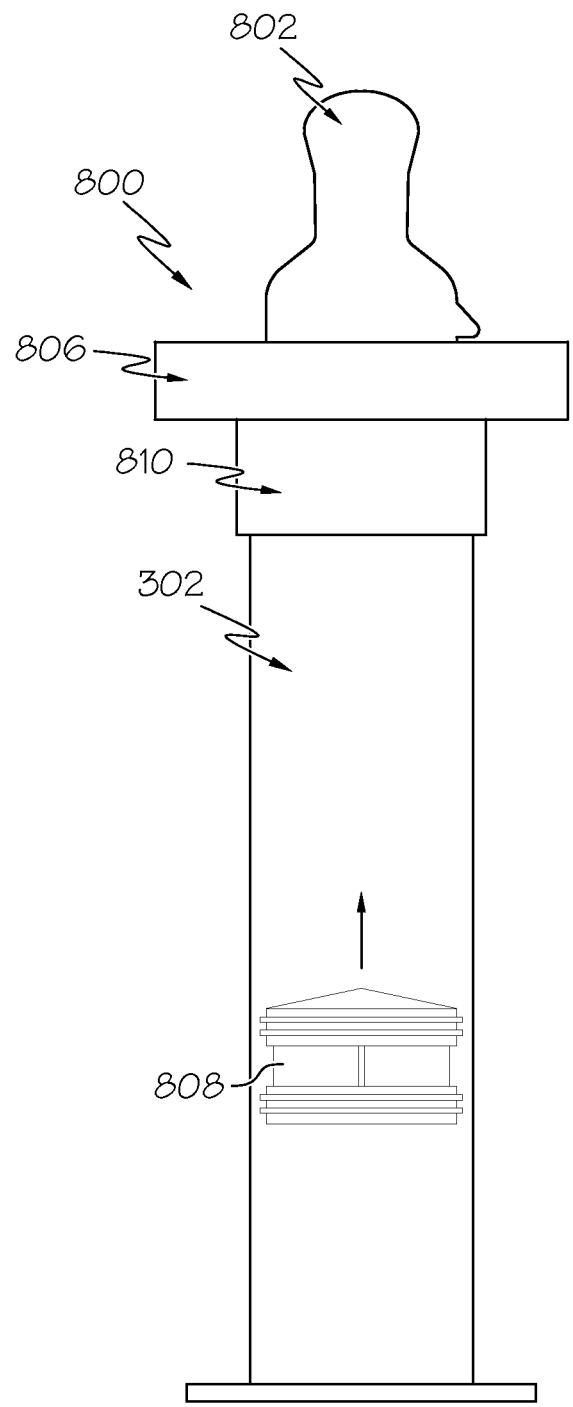
FIG. 27 is a side view of a nipple adaptor according to another example embodiment of the present invention, shown secured to a nipple and the syringe body of FIG. 3.
Figure 28:
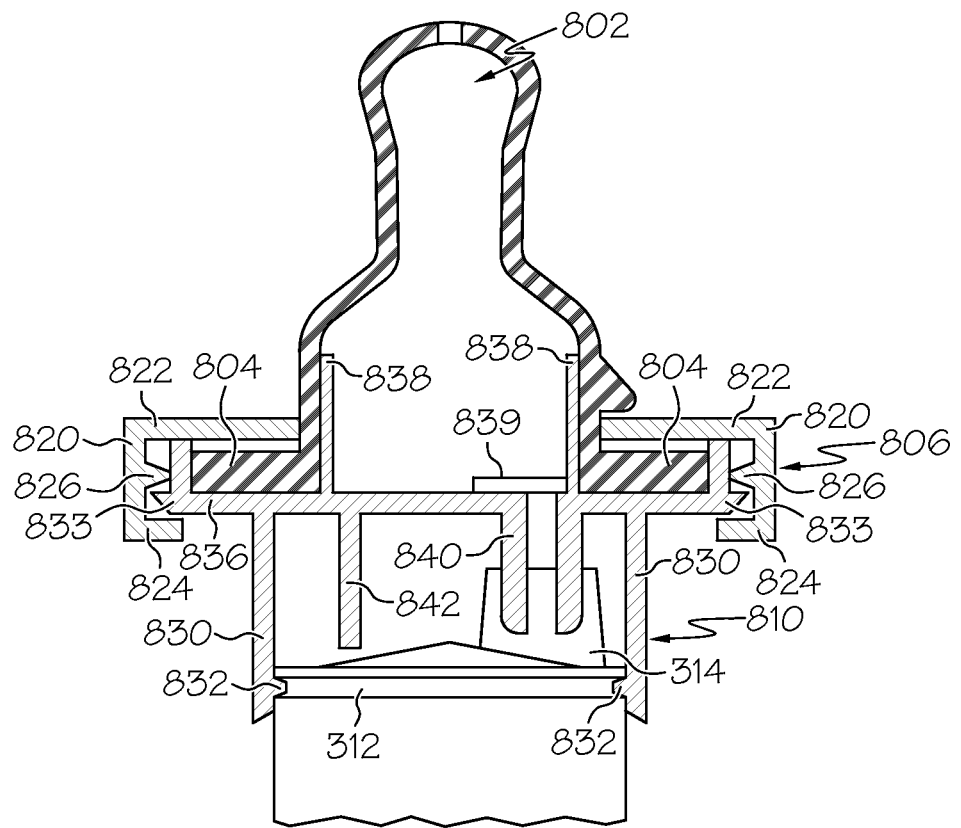
FIG. 28 is a cross-sectional view of the nipple adaptor of FIG. 27.
Figure 28:
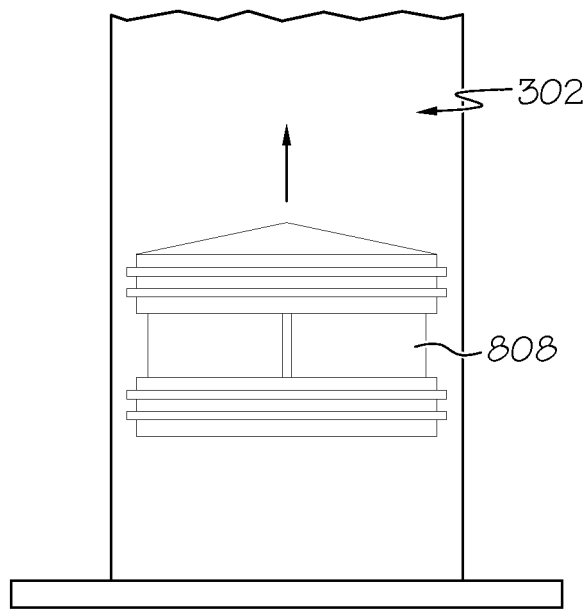
Figure 29:
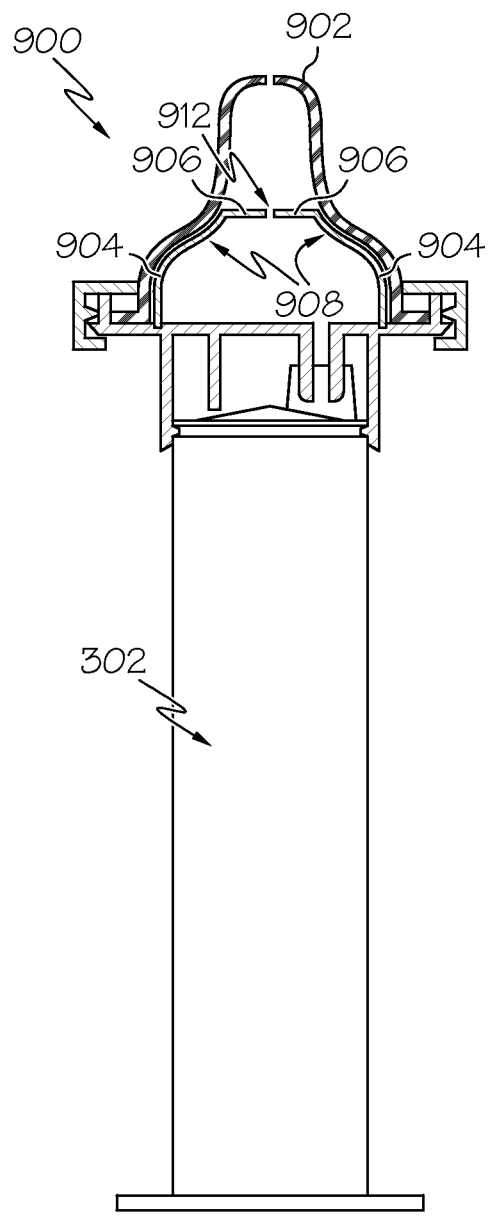
FIG. 29 is a cross-sectional view of a second alternative example embodiment nipple adaptor according to another example embodiment of the present invention shown secured to an alternative nipple and the syringe body of FIG. 3.

FIGS. 27-29 show a dispensing adaptor 810 for securing a nipple attachment to the syringe body 302. The nipple attachment 800 includes a flexible nipple 802, for example an Abbot®, or Evenflo® brand nipple. The nipple 802 has a circumferential lip 804 that is secured between a threaded collar/ring 806 and an adaptor 810. When the nipple 802, threaded collar/ring 806 and adaptor 810 are secured to the syringe body 302, liquid contained within the syringe body can be forced outward through the nipple.

The threaded collar/ring 806 has a circumferential top surface 822 with a central aperture through which the nipple 802 extends upwardly. The handle 806 also has a circumferential underhang 824 positioned in a parallel plane beneath the top surface 822. A grip surface 820 extends circumferentially perpendicular between the top surface 822 and the underhang 824. A fastening mechanism 826, for example a snap-on feature, extends along the inner facing surface of the vertical grip surface 820. The snap-on feature 826 can secure to a corresponding snap-on on the adaptor 810, as described below. Preferably, the threaded collar/ring 806 is integrally molded as a unitary structure.

The depicted adaptor 810 includes an outer collar 830 positioned perpendicularly to a shelf 836. The collar 830 preferably has an elliptical circumference similar to the caps 500, 410 described above. The shelf 836 can have a generally circular circumference. As depicted, the shelf 836 can have a circumferential wall extending perpendicularly away from the edge of the circular shelf and a fastening mechanism 833, for example a snap-on feature, to cooperate with the fastening mechanism 826. The lip 804 of the nipple 802 is secured between the lid 822 and the shelf 836. Several ribs 838 extend perpendicularly upward from the shelf 836 and align with the interior surface of the nipple 802 to prevent the nipple 802 from collapsing during use. Alternatively, the ribs 838 can be a single circumferential structure that lines the entirety of the internal surface of the nipple 802.

FIG. 29 presents an alternative nipple attachment 900 to that shown in FIG. 28. The attachment embodiment 900 has a generally-consistent construction, design and function as the attachment 810, but includes an extended anti-collapse seal 908 instead of the anti-collapse ribs 838. The anti-collapse seal 908 includes a support section 904 that conforms to the shape of the nipple 802 and a barrier section 906 that extends from the ends of the support section. The anti-collapse seal 908 includes a resiliently-sealable aperture 912 near the center of the barrier. The anti-collapse seal 908 ensures an air-tight seal that allows for use without a movable plunger 808.

Similarly to the caps 500, 410 described above, the adaptor collar 830 is preferably constructed of resiliently-flexible material, for example plastic and has an elliptical shape with a major (X) axis and a minor (Y) axis. In use, pinching pressure applied simultaneously to the opposing ends of the major (X) axis of the adaptor collar 830 causes the resiliently-flexible collar to change its shape to shorten the major (X) axis and lengthen the minor (Y) axis. When this simultaneous pressure is released, the resiliently-flexible collar 830 returns to the pre-pressure relaxed state and dimensions.

A support 842, similar to the cap 500 described above, extends downardly from the shelf 836. The support 842 can have a semi-circular wall shape with a disconnect and the support 842 can be positioned with respect to the shelf 836 such that an enteral-only tip 840 is positioned within the disconnect of the semi-circular wall shape. The enteral-only tip 840 extends from the underside of the shelf 836, as depicted. The enteral-only tip 840 forms an air-tight interference or friction-fit seal with the chimney insert 318, similarly to the plug 516 described above. A cover seal 839 can extend across the opening of the enteral-only tip 840 to prevent entry and exit of ambient air with respect to the syringe body 302. The cover seal 839 ensures an air-tight seal that allows for use without a movable plunger 808. In use, when the enteral-only tip 840 is inserted into the chimney insert 318, a distal edge of the support 842 contacts the lid 304. This alignment of the support 842 and the lid 304 assists to prevent the enteral-only tip 840 from inserting an unwanted distance into the chimney 314. The semi-circular shape of the support 842 corresponds with the cone shape of the lid 304 to maintain an even distribution of support. The port 840 and support 842 can be aligned off-center along the major (X) axis within the adaptor collar 830.

A pair of teeth grips 832, similar in design, construction and function to the teeth 416, 514 described above, extend inwardly from the interior surface of the collar 830. As depicted, pair of teeth grips 832 can extend from diametrically opposed locations separated along the minor (Y) axis of the collar 830. Alternatively, additional pairs of teeth grips at alternative locations can be effective. The teeth grips 832 are preferably co-molded with the adaptor 810. The shape of the teeth grips 832 is designed to removably insert into the continuous groove 312 between the lid 304 and the syringe body 302. The resilient force of the collar 830 presses the teeth grips 832 into the continuous groove 312 when the collar is in a relaxed state, thus preventing the adaptor 810 from involuntary removal during use. Applying simultaneous inward pinching pressure opposing ends of the major (X) axis of the collar 830 elongates the minor (Y) axis and removes the teeth grips 832 out of the continuous groove 312 so that the adaptor 810 can be removed. The teeth grips 832 preferably inserted between the pair of ribs 306 in the continuous groove 312 to prevent the collar 830 from rotating within the groove.

Figure 30:
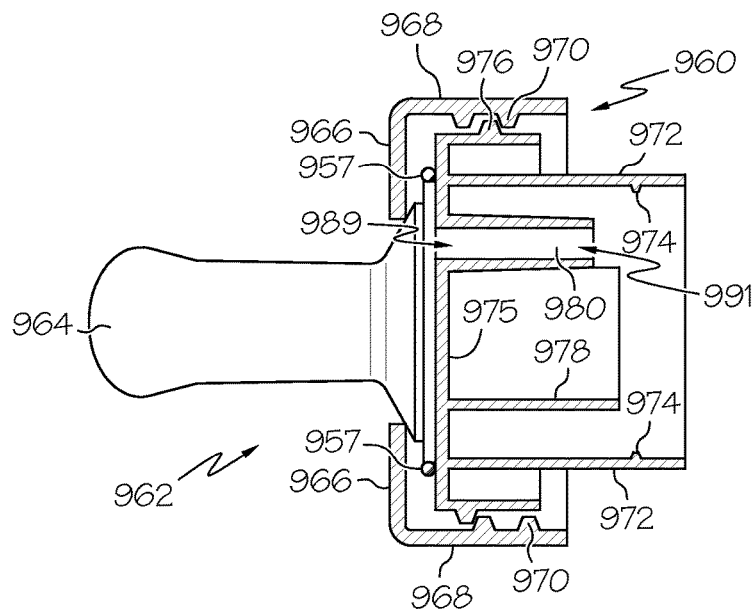
FIG. 30 is a cross-sectional view of a third alternative example embodiment nipple adaptor according to another example embodiment of the present invention, shown secured to an alternative nipple.
Figure 31:
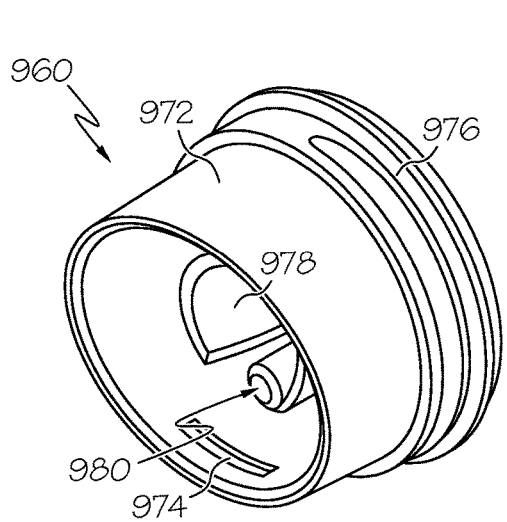
FIG. 31 is a perspective view of the nipple adaptor of FIG. 30.
Figure 32:
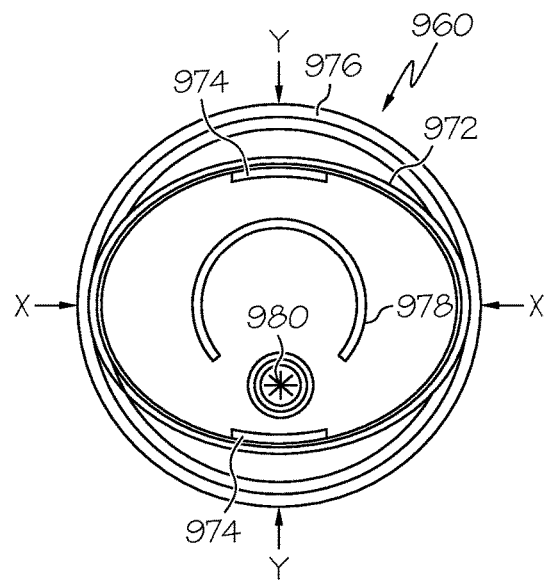
FIG. 32 is a bottom view of the nipple adaptor of FIG. 30.

Alternatively, as shown in FIGS. 30-32, a nipple attachment 962 with a nipple 964 secured to a handle can be secured to an alternative adaptor 960. The nipple 964 is secured beneath a circumferential lid 966 with a circumferential handle 968 having an internal threaded surface 970. The adaptor 960 has an outer wall with a corresponding circumferential threaded surface 976 that can secure to the handle threaded surface 970. The adaptor 960 includes a collar 972 that is positioned within the circumference of the outer wall circumferential threaded surface 976. The collar 972 has a greater height than the outer wall circumferential threaded surface 970. The collar 972 can have an elliptical circumference with a major (X) axis and a minor (Y) axis. Similarly to the breast-pump adaptor 704 described above, the nipple adaptor 960 has an elongated port 980 with a proximal opening 989 and a distal opening 991 extending from a shelf 975. The nipple adaptor 960 also has a support 978 that is depicted to have a semi-circular wall shape with a disconnect. As depicted, the port 980 is positioned within the disconnect of the support 978. Similarly to the alternative cap 500A, the port 980 and the support 978 can be centrally-aligned along the minor (Y) axis within the collar 972. The adaptor 960 can also include a raised platform or seal 957 secured with respect to the top surface and interfacing with the nipple 964. This raised platform or seal 957 can be a ring-shape constructed of flexible material, for example rubber or silicone. The seal 957 can have an adjustable dimension, for example diameter, and is preferably ribbed, to allow for venting of trapped air. The nipple 964 rests with respect to the raised platform or seal 957 so as to allow the venting of air as liquid passes through towards and outward from the nipple.

In use, the distal opening 991 of the port 980 inserts into the passageway 320 in the above-described chimney insert 318 until it forms a friction-fit similar to that with the enteral-only tip 400. The friction fit is air-tight and prevents unwanted material from entering or exiting the syringe body 302 during use.

The adaptor collar 972 is preferably constructed of resiliently-flexible material, for example plastic and has an elliptical shape with a major (X) axis and a minor (Y) axis. In use, pressure applied simultaneously to the opposing ends of the major (X) axis of the adaptor collar 972 causes the resiliently-flexible collar to change its shape to shorten the major (X) axis and lengthen the minor (Y) axis. When this simultaneous pressure is released, the resiliently-flexible collar 972 returns to the pre-pressure relaxed state and dimensions.

A pair of teeth grips 974 similar in design, construction and function to the teeth 416, 514 described above extend inwardly from the interior surface of the collar 972. As depicted, the pair of teeth grips 974 can extend from diametrically opposed locations separated along the minor (Y) axis of the collar 972. Alternatively, additional pairs of teeth grips at alternative locations can be effective. The teeth grips 974 are preferably co-molded with the adaptor 960. The shape of the teeth grips 974 is designed to removably insert into the continuous groove 312 between the lid 304 and the syringe body 302. The resilient force of the collar 830 presses the teeth grips 832 into the continuous groove 312 when the collar is in a relaxed state, thus preventing the adaptor 810 from involuntary removal during use. Applying simultaneous inward pinching pressure opposing ends of the major (X) axis of the collar 830 elongates the minor (Y) axis and removes the teeth grips 832 out of the continuous groove 312 so that the adaptor 810 can be removed. The teeth grips 832 preferably inserted between the pair of ribs 306 in the continuous groove 312 to prevent the collar 830 from rotating within the groove.

While the invention has been described with reference to preferred and example embodiments, it will be understood by those skilled in the art that a variety of modifications, additions and deletions are within the scope of the invention, as defined by the following claims.

What is claimed is:

1. A system for collection, storage and delivery of fluid comprising:
   a variable volume container comprising a container body and a plunger, the container body including an outside surface and defining an internal cavity therein, the container body including an open first end and a second end, the plunger being receivable within the open end of the container body and operable to be advanced and retracted within the internal cavity, the second end of the container body having an endwall with a container port extending therethrough and in fluid communication with the internal cavity;
   a collection adaptor comprising a mouth region, a base region, and a transition region between the mouth and base regions, the base region comprising a first container coupling configured for releasable attachment to the second end of the container body and a collection port configured for releasable engagement with the container port of the variable volume container, wherein the collection port of the collection adaptor is configured to form a vented connection with the container port of the variable volume container when the collection port is engaged with the container port to allow release of air from the internal cavity as the fluid is collected therein; and
   a dispensing adaptor comprising a shelf at a first end thereof and having a collar extending from the shelf towards a second end, the collar comprising a second container coupling configured for releasable attachment to the second end of the container body, the dispensing adaptor further comprising a dispensing port extending from the shelf toward the second end thereof and configured for releasable engagement with the container port of the variable volume container;
   wherein the collection adaptor and the dispensing adapter are alternatively attached to the container body for collection and delivery of fluid, respectively, to and from the variable volume container.

2. The system of claim 1, wherein the container port comprises a reclosable seal to prevent contaminants from entering the internal cavity of the variable volume container when closed, and to allow fluid delivery through the container port when the seal is opened by engagement of the collection port or the dispensing port with the container port.

3. The system of claim 1, wherein the collection port of the collection adaptor has an outside diameter that is smaller than an inside diameter of the container port to form the vented connection with the container port of the variable volume container when the collection port is engaged with the container port to allow release of air from the internal cavity as fluid is collected therein.

4. The system of claim 1, wherein the dispensing port of the dispensing adaptor is configured to form a sealed connection with the container port of the variable volume container when the dispensing port is engaged with the container port.

5. The system of claim 1, wherein the base region of the collection adaptor comprises a generally elliptical circumference.

6. The system of claim 1, wherein the dispensing adaptor further comprises an outer wall having a threaded surface configured for removable attachment to a nipple.

7. A system for collecting, containing and dispensing fluids comprising:
   a variable volume container comprising a syringe body and a plunger, the syringe body defining an internal chamber and the plunger being translationally movable within the internal chamber to vary a contained volume within the internal chamber, the syringe body further comprising a syringe port in fluid communication with the internal chamber;
   a collection adaptor for collection of fluids into the internal chamber of the syringe body, the collection adaptor comprising a first end having a first coupling configured for releasable attachment to the syringe body, a second end having a second coupling configured for releasable attachment to a breast pump, and a transition region between the first and second ends, and a collection port configured to form a vented connection with the syringe port of the variable volume container when the collection port is engaged with the syringe port to allow release of air from the internal chamber as fluid is collected therein; and
   a dispensing adaptor for dispensing of fluids from the internal chamber of the syringe body, the dispensing adaptor comprising a first end for releasable attachment to the syringe body, a second end for removably coupling to a nipple, and a dispensing port configured to form a sealed connection with the syringe port of the variable volume container when the dispensing port is engaged with the syringe port.

8. The system of claim 7, wherein the second end of the collection adaptor comprises a threaded portion configured for removable connection with the breast pump.

9. The system of claim 7, wherein the second end of the dispensing adaptor comprises a threaded surface for removable connection with the nipple.

10. The system of claim 7, further comprising a reclosable seal within the syringe port to prevent contaminants from entering the internal chamber of the syringe body when the seal is closed, and to allow fluid delivery through the syringe port when the seal is opened by engagement of the collection port or the dispensing port with the syringe port.

11. A system for collecting, containing and dispensing enteral fluid, the system comprising:
   a syringe comprising a syringe body and a plunger, the syringe body defining an internal chamber, and the plunger being movably mounted within the internal chamber of the syringe body, the syringe body comprising a syringe port providing fluid communication to and from the internal chamber;
   a collection adaptor comprising a first collection adaptor coupling configured for removable attachment to the syringe, a second collection adaptor coupling configured for removable attachment to a breast pump, a transition region between the first collection adaptor coupling and the second collection adaptor coupling, and comprising a collection port for releasable engagement with the syringe port, wherein a vented connection is formed when the collection port is engaged with the syringe port to allow release of air from the internal chamber as the enteral fluid is collected therein; and
   a dispensing adaptor comprising a first dispensing adaptor coupling for removable attachment to the syringe, a second dispensing adaptor coupling for removable attachment to a nipple, and a dispensing port for releasable engagement with the syringe port.

12. The system of claim 11, wherein the collection port has an outside diameter smaller than an inside diameter of the syringe port.

13. The system of claim 11, wherein the dispensing port has an outside diameter forming a sealing fit with an inside diameter of the syringe port, whereby a sealed connection is provided when the dispensing port is engaged with the syringe port to dispense an enteral fluid from the internal chamber.

14. The system of claim 11, wherein the syringe port further comprises a reclosable seal to prevent contaminants from entering the internal chamber of the syringe body when the seal is closed, and to allow fluid delivery through the syringe port when the seal is opened by engagement of the collection port or the dispensing port with the syringe port.

15. The system of claim 11, wherein the transition region of the collection adaptor comprises a tapered funnel portion.

16. The system of claim 11, wherein the first collection adaptor coupling comprises a resiliently flexible elliptical collar, and the second collection adaptor coupling comprises a threaded coupling.

17. The system of claim 11, wherein the first dispensing adaptor coupling comprises a resiliently flexible elliptical collar, and the second dispensing adaptor coupling comprises a threaded coupling.

18. The system of claim 11, wherein the second collection adaptor coupling includes a threaded portion configured for removable connection with cooperating threaded portions of the breast pump.

\* \* \* \* \*